(12) United States Patent
Calenoff et al.

(10) Patent No.: US 6,892,140 B1
(45) Date of Patent: May 10, 2005

(54) IMMUNOGENIC CANCER PEPTIDES AND USES THEREOF

(75) Inventors: Emanuel Calenoff, Chicago, IL (US); Charles Ditlow, Chicago, IL (US)

(73) Assignee: Enteron, Inc., Oak Brook, IL (US)

(*) Notice: Subject to any disclaimer, the term of this patent is extended or adjusted under 35 U.S.C. 154(b) by 320 days.

(21) Appl. No.: 09/723,307

(22) Filed: Nov. 27, 2000

(51) Int. Cl.[7] .................. G01N 33/48; A61K 38/14; A61K 45/00; A61K 39/00; A01N 63/00

(52) U.S. Cl. .................. 702/19; 424/85.1; 424/85.2; 424/93.71; 424/184.1; 530/322; 702/20

(58) Field of Search .................. 424/85.1, 85.2, 424/85.6, 85.7, 93.71, 184.1; 530/322; 702/19, 20

(56) References Cited

U.S. PATENT DOCUMENTS

| | | |
|---|---|---|
| 4,399,216 A | 8/1983 | Axel et al. |
| 4,585,742 A | 4/1986 | Bernal |
| 5,194,254 A | 3/1993 | Barber et al. |
| 5,342,774 A | 8/1994 | Boon et al. |
| 5,593,972 A | 1/1997 | Weiner et al. |
| 5,616,477 A | 4/1997 | Price |
| 5,620,955 A | 4/1997 | Knight et al. |
| 5,736,517 A | 4/1998 | Bogden et al. |
| 5,750,110 A | 5/1998 | Prieels et al. |
| 5,763,164 A | 6/1998 | Calenoff |
| 5,770,721 A | 6/1998 | Ershov et al. |
| 5,772,997 A | 6/1998 | Hudziak et al. |
| 5,817,637 A | 10/1998 | Weiner et al. |
| 5,830,876 A | 11/1998 | Weiner et al. |
| 5,837,251 A | 11/1998 | Srivastava |
| 5,851,756 A | 12/1998 | Steinman et al. |
| 5,861,247 A | 1/1999 | Mirzabekov et al. |
| 5,871,756 A | 2/1999 | Jeffcoat et al. |
| 5,876,735 A | 3/1999 | Reed |
| 5,876,966 A | 3/1999 | Reed |
| 5,942,235 A | 8/1999 | Paoletti |
| 5,962,320 A | 10/1999 | Robinson |
| 5,981,505 A | 11/1999 | Weiner et al. |
| 5,981,706 A | 11/1999 | Wallen et al. |
| 5,985,270 A | 11/1999 | Srivastava |
| 5,997,873 A | 12/1999 | Srivastava |
| 6,013,268 A | 1/2000 | Reed |
| 6,030,618 A | 2/2000 | Srivastava |
| 6,051,237 A | 4/2000 | Paterson |
| 6,063,384 A | 5/2000 | Morrow et al. |
| 6,077,663 A | 6/2000 | Curiel et al. |
| 6,080,399 A | 6/2000 | Gajewski et al. |
| 6,080,409 A | 6/2000 | Laus et al. |
| 6,106,829 A | 8/2000 | He et al. |
| 6,136,315 A | 10/2000 | Srivastava |

OTHER PUBLICATIONS

Taylor–Papadimitriou et al., Exploiting altered glycosylation patterns in cancer; progress and challenges in diagnosis and therapy. TIBTECH, Jun. 1994, vol. 12, pp. 227–233.*
Hopp et al., Prediction of protein antigenic determinants from amino acid sdquences. Proc. Natl. Acad. Sci. USA, vol. 78, pp. 3824–3828, 1981.*

Barratt–Boyes, S.M., et al. (1998) "Chimpanzee Dendritic Cells Derived In Vitro from Blood Monocytes and Pulsed with Antigen Elicit Specific Immune Responses In Vivo. " Third Keystone Symposium on Cellular Immunology and the Immunotherapy of Cancer Antigen Processing and Presentation. *J. Immunother.* 21(2): 142–148.

Begum, N.A. et al. (1995) "Differential Display and Integrin Alpha 6 Messenger RNA Overexpression in Hepatocellular Carcinoma." *Hepatology.* 22(5): 1447–1455.

Bonkhoff, H. (1998) "Analytical Molecular Pathology of Epithelial–Stromal Interactions in the Normal and Neoplastic Prostate." *Anal. Quant. Cytol. Histol.* 20(5): 437–442.

Brame, C.J. et al. (1999) "Identification of Extremely Reactive γ–Ketoaldehydes (Isolevuglandins) as Products of the Isoprostane Pathway and Characterization of Their Lysyl Protein Adducts." *J. Biol. Chem.* 274(19): 1319–1346.

Bryden, A.A.G., et al. (1999) "Paradoxical Expression of E–Cadherin in Prostatic Bone Metastases." *BJU Int.* 84(9): 1032–1034.

Cheever, M.A., et al. (1997) "Therapy with Cultured T Cells: Principles Revisited." *Immunol Rev.* 157: 177–194.

Cress, A.E., et al. (1995) "The α6β1 and α6β4 Integrins in Human Prostate Cancer Progression." *Cancer Metastasis Revs.* 14(3): 219–228.

Damiano, J.S. et al., (1999) "Cell Adhesion Mediated Drug Resistance (CAM–DR): Role of Integrins and Resistance to Apoptosis in Human Myeloma Cell Lines." *Blood* 93(5): 1658–1667.

Damjanovich, L. et al. (1997) "Integrin Expression on Normal and Neoplastic Human Breast Epithelium." *Acta Chir. Hung.* 36(1–4): 69–71.

Disis, M.L. et al. (1999) "Generation of Immunity to the HER–2/neu Oncogenic Protein in Patients with Breast and Ovarian Cancer using a Peptide–based Vaccine." *Clin. Cancer Res.* 5(6): 1289–1297.

Disis, M.L., et al. (1997) "HER–2/neu Protein: A Target for Antigen–Specific Immunotherapy of Human Cancer." *Advances in Cancer Research* 344–370.

Disis, M.L. et al. (1998) "HER–2/neu Oncogenic Protein: Issues in Vaccine Development." *Crit. Revs. Immunol.* 18(1–2): 37–45.

Disis, M.L. et al. (1998) "Human HER–2/neu Protein Immunization Circumvents Tolerance to Rat neu: A Vaccine Strategy for "Self" Tumour Antigens." *Immunology* 93(2): 192–199.

Dong, J–T., et al. (1996) "Down–Regulation of the KAII Metastasis Suppressor Gene during the Progression of Human Prostatic Cancer Infrequently Involves Gene Mutation or Allelic Loss." *Cancer Res.* 56(19): 4387–4390.

(Continued)

Primary Examiner—John Brusca
Assistant Examiner—Shubo Zhou
(74) Attorney, Agent, or Firm—Barnes & Thornburg

(57) ABSTRACT

This invention relates to novel general methods and compositions that provide cancer-specific or highly cancer-associated antigens useful for diagnosis and treatment of cancer.

1 Claim, 10 Drawing Sheets

OTHER PUBLICATIONS

Ekblom, M., et al. (1998) "Laminin Isoforms and Epithelial Development." *Ann. N.Y. Acad. Sci.* 857: 194–211.

Fauchère, J.L. et al. (1983) "Hydrophobic Parameters II of Amino–Acid Side Chains from the Partitioning of N–Acetyl–Amino–Acid Amides." *Eur. J. Med. Chem.* 18(4): 369–375.

Fleischmajer, R. et al. (1998) "There is Binding of Collagen IV to β1 Integrin during Early Skin Basement Membrane Assembly." *Ann. N.Y. Acad. Sci.* 857:212–227.

Fraga, S., et al. (1990) "Prediction of the Secondary Structure and Functional Sites of Major Histocompatibility Complex Molecules." *J. Mol. Recognit.* 3(2): 65–73.

Friedl, P., et al. (1998) "Integrins, Cell Matrix Interactions and Cell Migration Strategies: Fundamental Differences in Leukocytes and Tumor Cells." *Cell Adhes. Commun.* 6(2–3): 225–236.

Fudge, K., et al., (1994) "Immunohistochemistry Analysis of Platelet–derived Growth Factor A and B Chains and Platelet–derived Growth Factor α and β Receptor Expression in Benign Prostatic Hyperplasias and Gleason–graded Human Prostate Adenocarcinomas." *Mod. Pathol.* 7(5): 549–554.

Fujiwara, H. (1998) "Physiological Roles of Integrin $\alpha_6\beta_1$ in Ovarian Functions." *Harm. Res.* 50(2): 25–29.

Furukawa, F., et al. (1994) "Cadehrins in Cutaneous Biology," *J. Dermatol.* 21(11):802–813.

Gilewski, T., et al. (2000) "Vaccination of High–Risk Breast Cancer Patients with Mucin–1 (MUCI) Keyhole Limpet Hemocyanin Conjugate Plus QS–21[1]." *Clin. Cancer Res.* 6(5): 1693–1701.

Giri, D., et al. (1999) "Alterations in Expression of Basic Fibroblast Growth Factor (FGF) 2 and its Receptor FGFR–1 in Human Prostate Cancer[1]." *Clin. Cancer Res.* 5(5): 1063–1071.

Goldenberg, D.M. (1993) "Monoclonal Antibodies in Cancer Detection and Therapy." *Am. J. Med.* 94(3):297–312.

Grasso, A.W., et al. (1997) "ErbB Kinases and NDF Signaling in Human Prostate Cancer Cells." *Oncogene* 15(22): 2705–2716.

Henderson, R.A., et al. (1998) "Retroviral Expression of MUC–1 Human Tumor Antigen with Intact Repeat Structure and Capacity to Elicit Immunity In Vivo." Third Keystone Symposium on Cellular Immunology and the Immunotherapy of Cancer. Tumor Antigens Regonized by T Cells. *J. Immunother.* 21(4): 247–256.

Hopp, T.P. et al. (1981) "Prediction of Protein Antigenic Determinants from Amino Acid Sequences." *Proc. Natl. Acad. Sci. USA.* 78(6): 3824–3828.

Hudziak, R.M., et al. (1989) "p185[HER3] Monoclonal Antibody Has Antiproliferative Effects in Vitro and Sensitizes Human Breast Tumor Cells to Tumor Necrosis Factor." *Mol. Cell Biol.* 9(3): 1165–1172.

Hussain, R., et al., (1996) "Structure–Function Correlation and Biostability of Antibody CDR–Derived Peptides as Tumour Imaging Agents." *Biomed. Pept. Proteins Nucleic Acids* 2(3): 67–70.

Katsura, M. et al. (1998) "Overexpression of CD44 Variants 6 and 7 in Human Endometrial Cancer." *Gynecol. Oncol.* 71(2): 185–189.

Kramer, G., et al. (1995) "High Expression of A CD38–Like Molecule in Normal Prostatic Epithelium and its Differential Loss in Benign and Malignant Disease." *J. Urol.* 154(5): 1636–1641.

Liapsis, H., et al., (1996) "Integrin $\alpha_v\beta_3$ Expression by Bone Residing Breast Cancer Metastases." *Diagn. Mol. Pathol.* 5(2): 127–135.

Lohi, J., et al. (1998) "Neoexpression of the Epithelial Adhesion Complex Antigens Thyroid Tumours is Associated with Proliferation and Squamous Differentiation Markers." *J. Pathol.* 184(2): 191–196.

Luo, W., et al. (1999) "Tumor–suppressive Activity of CD66a in Prostate Cancer," *Cancer Gene Ther.* 6(4): 313–321.

Parker, J.M.R., et al. (1986) "New Hydrophilicity Scale Derived from High–Performance Liquid Chromatography Peptide Retention Data: Correlation of Predicted Surface Residues with Antigenicity and X–ray–Derived Accessible Sites." *Biochemistry* 25: 5425–5432.

Rabinovitz, I., et al. (1995) "Integrin α6 Expression in Human Prostate Carcinoma Cells is Associated with a Migratory and Invasive Phenotype in vitro and in vivo." *Clin. Exp. Metastasis* 13(6): 481–491.

Rokhlin. O.W., et al. (1997) "Fas–mediated Apoptosis in Human Prostatic Carcinoma Cell Lines." *Cancer Res.* 57(9): 1758–1768.

Romanov, V.I., et al. (1999) "RGD–Recognizing Integrins Mediate Interactions of Human Prostate Carcinoma Cells with Endothelial Cells In Vitro." *Prostate* 39(2): 108–118.

Ruoslahti, E. (1997) "Integrins as Signaling Molecules and Targets for Tumor Therapy." *Kidney Int.* 51(5): 1413–1417.

Shamsi, F.A., et al. (1998) "Immunological Evidence for Methylglyoxal–derived Modifications in Vivo." *J. of Biol. Chem.* 273(12): 6928–6936.

Shamsi, F.A., et al. (1998) "Superparamagnetic Iron Oxide Particles (SH U 555 A): Evaluation of Efficacy in Three Doses for Hepatic MR Imaging[1]." *Radiology* 206(2): 365–371.

Suzuki, K. et al. (1999) "Reduced Substratum Adhesion and Decreased Expressions of β1 and β4 Integrins in Human Breast Cancer Cells with a Property of Anchorage–Independent Growth." *Int. J. Oncol.* 14(5): 897–904.

Takahashi, S., et al. (1998) "Relationship between CD44 Expression and Differentiation of Human Prostate Adenocarcinomas." *Cancer Letts.* 129(1): 97–102.

To, S.Y.C., et al., (1992) "Monoclonal Antibody–Coated Magnetite Particles as Contrast Agents for MR Imaging and Laser Therapy of Human Tumors." *J. Cin. Laser Med. Surg.* 10(3): 159–169.

Tozawa, K. (1996) "Activation of Nuclear Factor–x B and Control of the Expression of Cell Adhesion Molecules in Human Prostate Cancer Cells." *Nipon Hinyokika Gakkai Zasshi* 87(9): 1082–1091.

Tran. N.L., et al. (1999) "N–Cadherin Expression in Human Prostate Carcinoma Cell Lines." *Am. J. Pathol.* 155(3): 787–798.

Tsimikas, S., et al. (1999) "Radiolabeled MDA2, an Oxidation–Specific, Monoclonal Antibody, Identifies Native Atherosclerotic Lesions in Vivo." *J. Nucl. Cardiol.* 6(1): 41–53.

Watanabe, M., et al. (1999) "Progression–linked Overexpression of c–Met in Prostatic Intraepithelial Neoplasia and Latent as well as Clinical Prostate Cancers." *Cancer Letts.* 141(1–2): 173–178.

Zheng, Duo–Qi, et al. (1999) "Prostatic Carcinoma Cell Migration via $\alpha_v\beta_3$ Integrin Is Modulated by a Focal Adhesion Kinase Pathway[1]. " *Cancer Res.* 59(7): 1655–1664.

\* cited by examiner

Figure 1

1    mrpsgtagaallallaalcpasraleekkvcggtsnkltqlgtfedhflslqrmfnncev
61   vlgnleityvqrnydlsflktiqevagyvlialntveriplenlqiirgnmyyensyala
121  vlsnydaNktglkelpmrnlqeilhgavrfsnnpalcnvesiqwrdivssdflsnmsmdf
181  qnhlgscqkcdpscpNgscwgageencqkltkiicaqqcsgrcrgkspsdcchnqcaagc
241  tgpresdclvcrkfrdeatckdtcpplmlynpttyqmdvnpegkysfgatcvkkcprnyv
301  vtdhgscvracgadsyemeedgvrkckkcegpcrkvcngigigefkdslsiNatnikhfk
361  NctsisgdlhilpvafrgdsfthtppldpqeldilktvkeitgflliqawpeNrtdlhaf
421  enleiirgrtkqhgqfslavvslNitslglrslkeisdgdviisgnknlcyantinwkkl
481  fgtsgqktkiisnrgensckatgqvchalcspegcwgpeprdcvscrNvsrgrecvdkcn
541  llegeprefvenseciqchpeclpqamNitctgrgpdnciqcahyidgphcvktcpagvm
601  geNntlvwkyadaghvchlchpNctygctgpglegcptngpkipsiatgmvgallIllvv
661  algiglfmrrrhivrkrtlrrllqerelvepltpsgeapnqallrilketefkkikvlgs
721  gafgtvykglwipegekvkipvaikelreatspkankeildeayvmasvdnphvcrllgi
781  cltstvqlitqlmpfgclldyvrehkdnigsqyllnwcvqiakgmnyledrrlvhrdlaa
841  rnvlvktpqhvkitdfglakllgaeekeyhaeggkvpikwmalesilhriythqsdvwsy
901  gvtvwelmtfgskpydgipaseissilekgerlpqppictidvymimvkcwmidadsrpk
961  frelliefskmardpqrylviqgdermhlpsptdsnfyralmdeedmddvvdadeylipq
1021 qgffsspstsrtpllsslsatsnnstvacidrnglqscpikedsflqryssdptgalted
1081 siddtfipvpeyinqsvpkrpagsvqnpvyhnqplnpapsrdphyqdphstavgnpeyln
1141 tvqptcvnstfdspahwaqkgshqisldnpdyqqdffpkeakpngifkgstaenaeylrv
1201 apqssefiga (SEQ ID NO: 67)

Figure 2

| Amino Acid Sequence Number | Peptide Sequence |
|---|---|
| 126 through 131 | daNktg |
| 126 through 133 | daNkTglk |
| 411 through 416 | peNrtd |
| 411 through 418 | peNrTdlh |
| 467 through 471 | rNvsr |
| 467 through 473 | rNvSrgr (portions of SEQ ID NO: 67) |

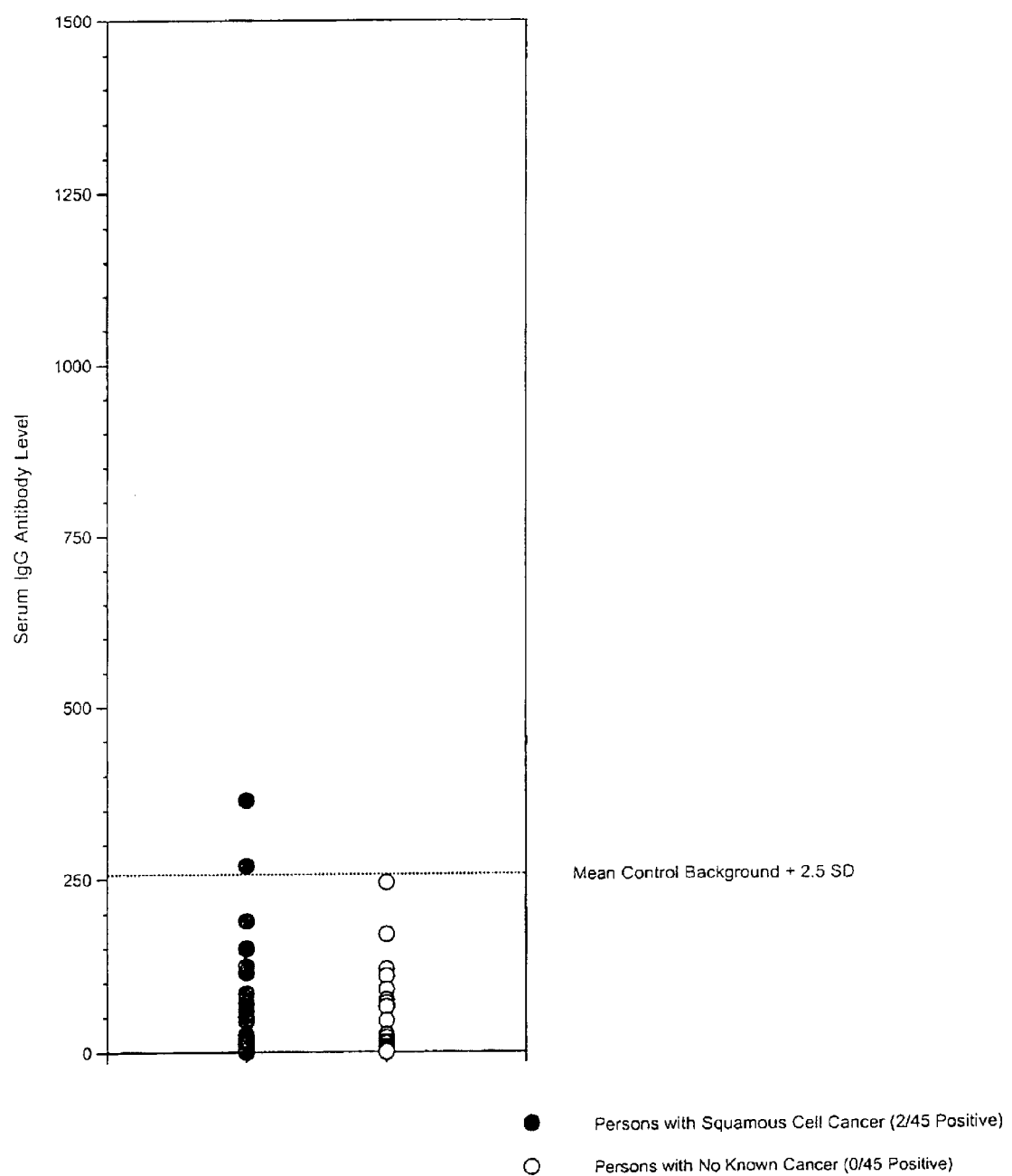
Figure 3a: Screening Result Using EGFR Peptide rNvsr (portions of SEQ ID NO: 67)

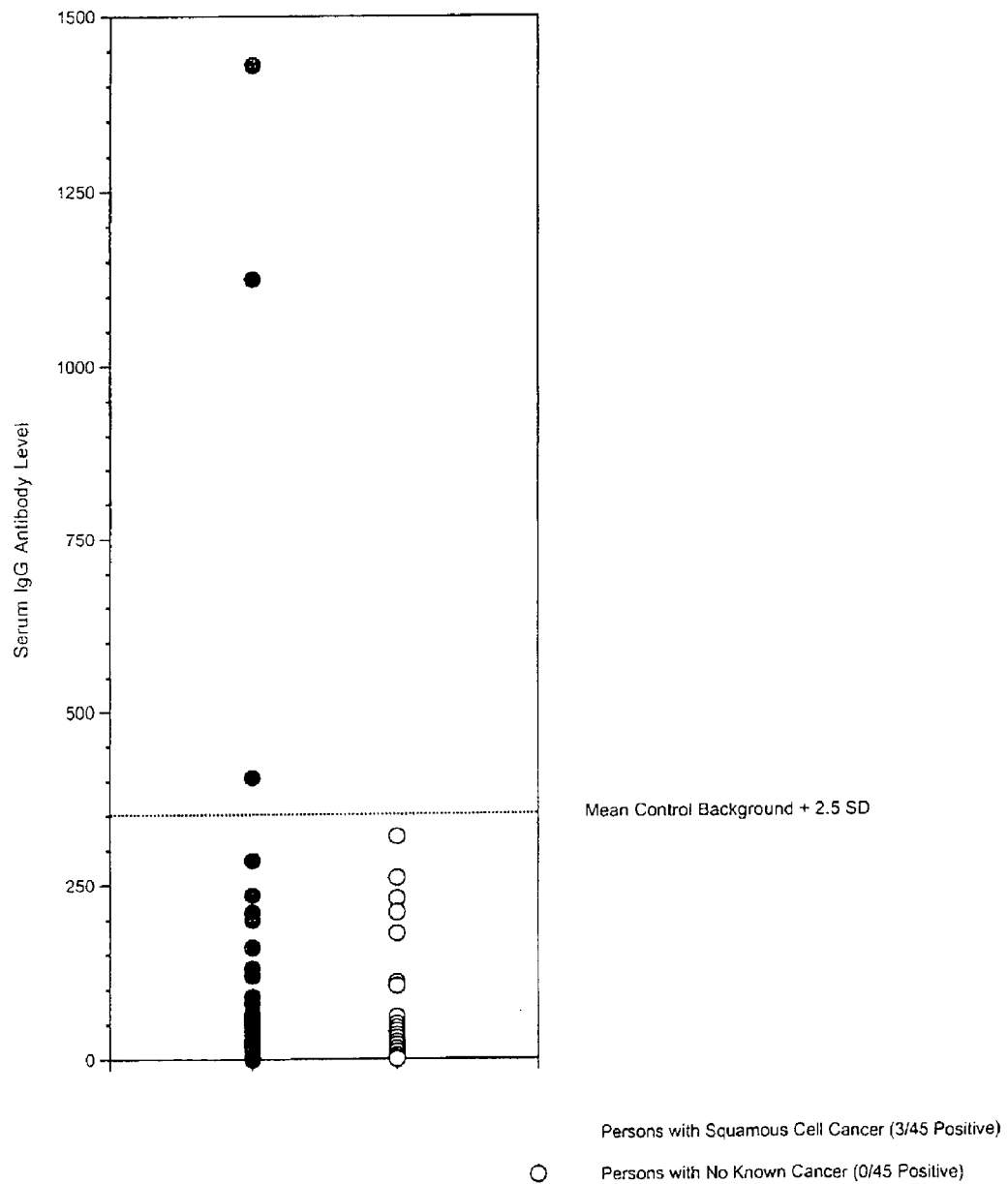

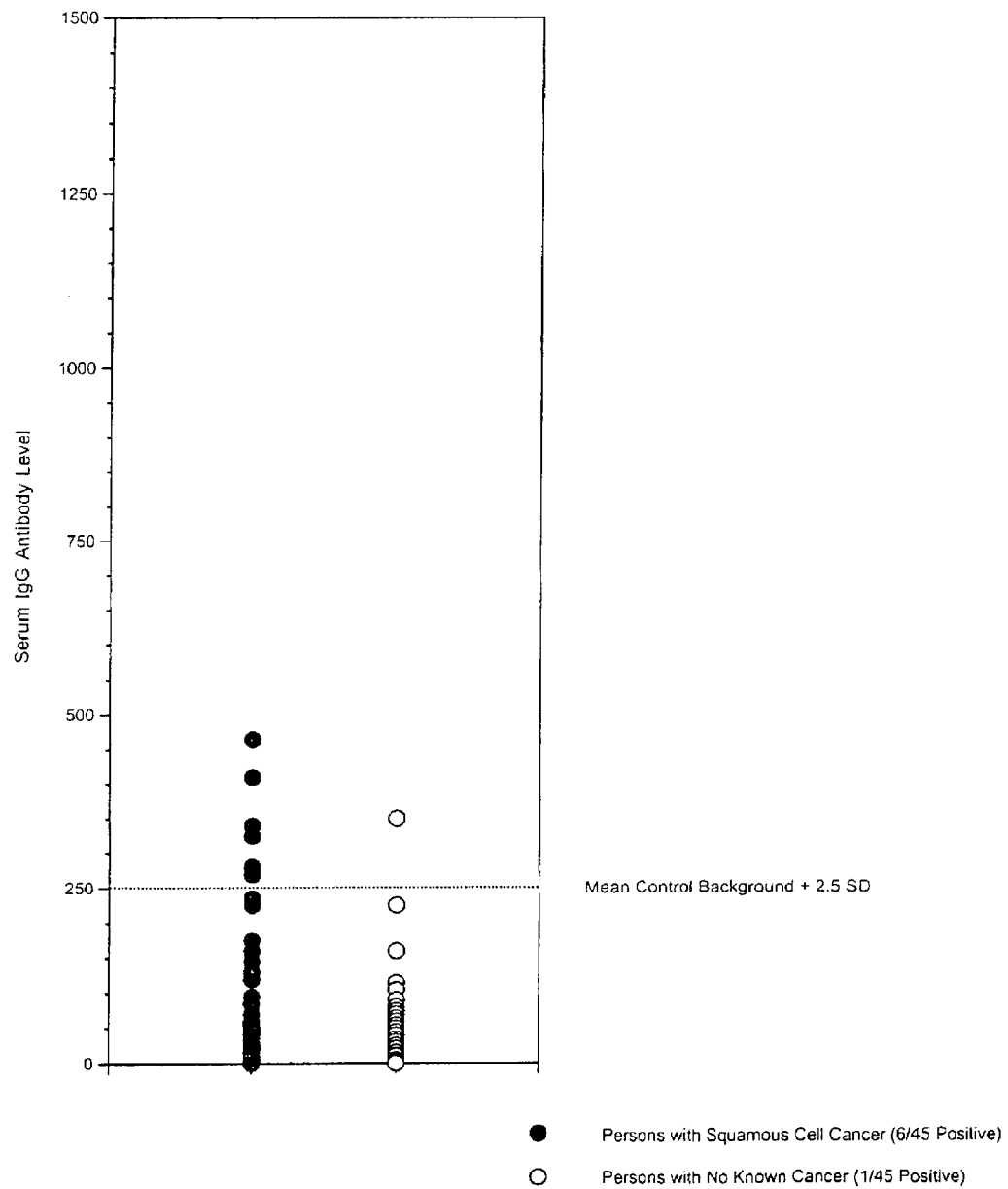

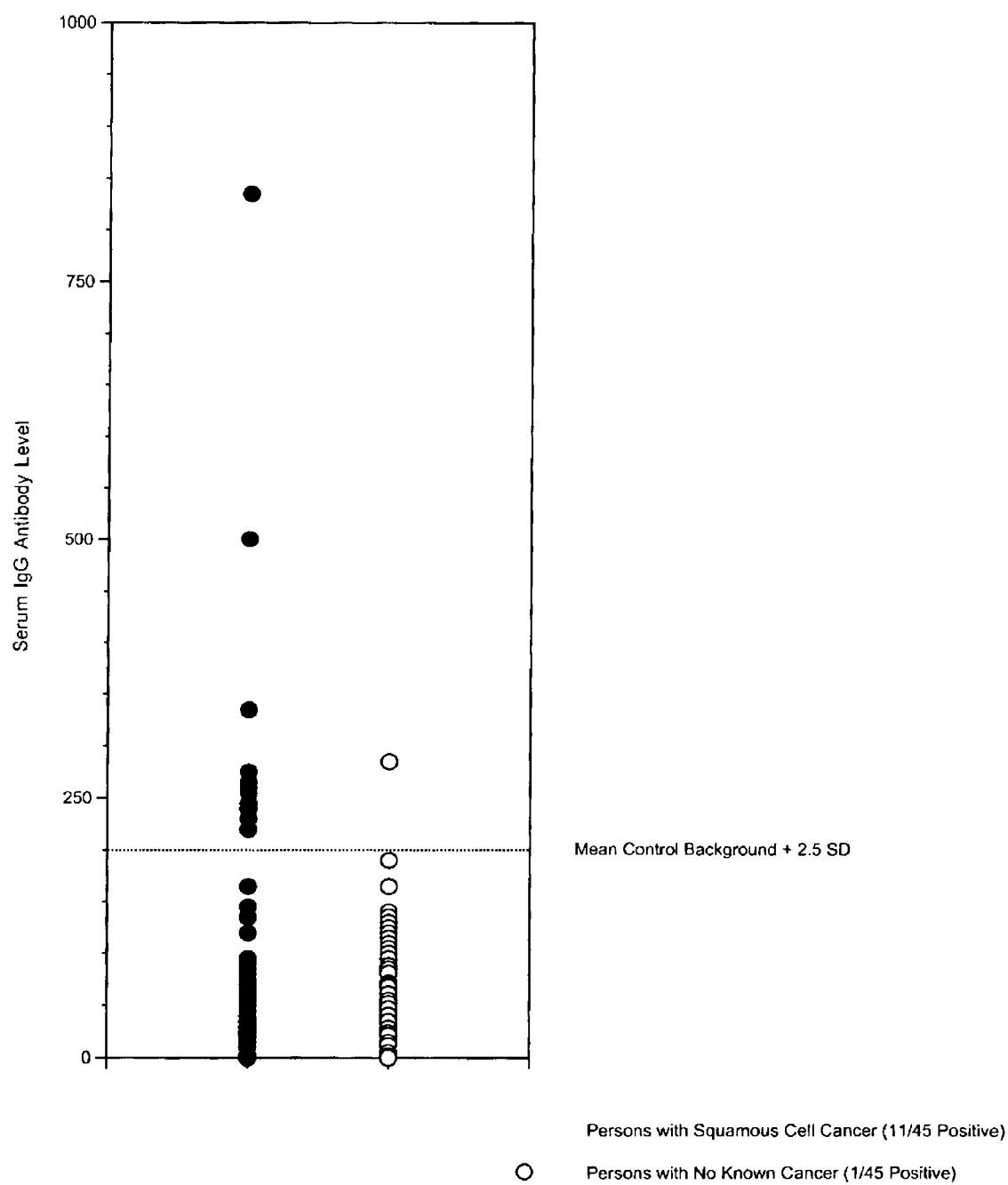
Figure 5: Serum Antibody Levels Obtained with 4 Biotinylated Peptides Used as Test Antigen

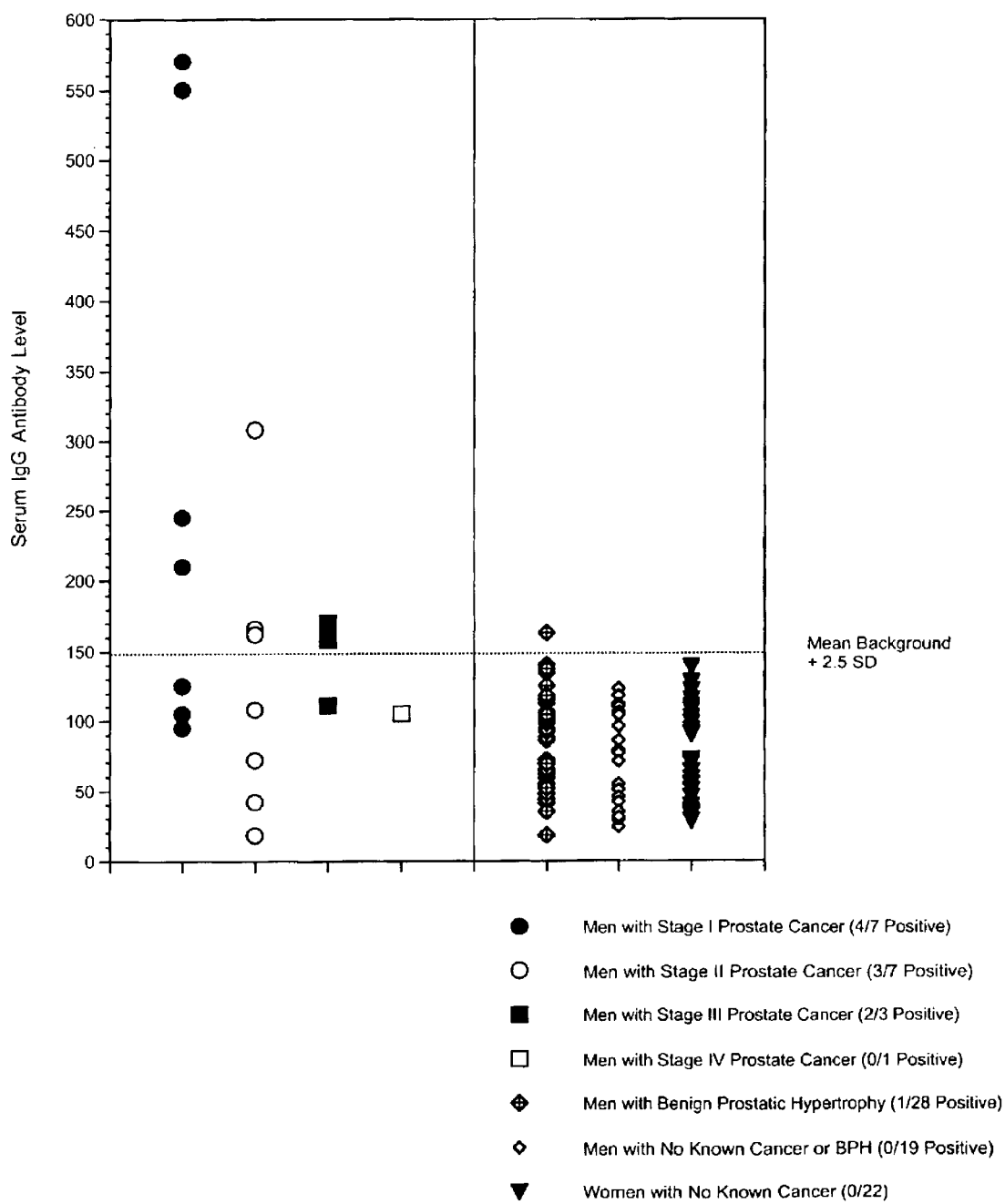

IMMUNOGENIC CANCER PEPTIDES AND USES THEREOF

This invention relates to novel general methods and compositions that provide cancer-specific or highly cancer-associated antigens useful for diagnosis and treatment of cancer.

BACKGROUND

The utilization of cancer-specific antigens and molecular markers in the diagnosis and treatment of malignant tumors is a goal of medical professionals. The realization of this goal has been advanced by the use of in vivo animal and in-vitro model systems in order to map out the relevant steps of a cancer-specific immune response and also the steps required for its use in cancer therapy. Methods which utilize cancer-specific and/or cancer-associated markers for diagnosis and therapy have been reported, but the principal shortcoming preventing the implementation of these methods has been the paucity of cancer-specific or highly cancer-associated antigens and other markers of cancer in humans.

Some progress in obtaining candidates for cancer-specific or highly cancer associated antigens for cancer diagnosis and treatment includes the construction of synthetic peptides, for example, for the production of antibodies specific for the peptides, where the peptides are potentially useful as markers. For example, different epitopes have been found to be associated with mucins from malignant cells, in contrast to mucins in non-malignant cells. Aberrant glycosylation has been found in some peptides from tumors.

Vaccines and immunotherapies using specific domains of membrane proteins have been reported to be more effective than vaccines and immunotherapy using entire glycoproteins.

At present, not enough cancer antigens or markers are available for use in implementing robust cancer diagnostic or therapeutic methods in humans. Human cancer antigens and markers described to date are either inadequate or too few in number to provide useful clinical tools.

For example, the MAGE family of antigens described by Boon et al. (1994) are reported to be cancer-associated antigens. Cancer-associated antigens are those expressed in greater quantity in molecules in or on, or derived from cancer cells, but are also concurrently expressed in molecules from normal cells. This duality complicates therapeutic utility of the antigens for vaccines and antibodies where positive effects are dependent upon reaching a therapeutic dose before a toxic dose level is realized. Other limitations of the MAGE antigens are that they are also intracellular cancer antigens thus greatly diminishing their utility for cancer cell targeting which is more effective for cell surface antigens. Intracellular antigens serve as poor localizing targets for immunotherapy, targeted cytotoxic therapeutic agents, cell receptor blocking agents, other cell-surface disruptive agents, and for diagnostic imaging. They are poor immunogenic targets for eliciting a measurable immune response. Their release for direct quantification is unpredictable because cancer cell disruption is required.

Cheever et al.(1997a,b) have described the potential diagnostic and therapeutic use of oncogenic proteins which are expressed by both cancer and normal cells. They describe using oncogenic proteins with site-specific mutations as the cancer-specific antigens. However, the oncogenic proteins cited by Cheever, designated the p21 proteins, are intracellular and thus share the drawbacks of other intracellular antigens, that is, cannot the detected on cell surfaces. Furthermore, mutated expression is not always manifested by expressed oncogenic proteins in all cancer cells, thus leaving some cells to express oncogenic proteins which are subject to self-recognition and are thus poorly immunogenic.

Cheever's other example, the erbB-2 epidermal growth factor receptor, also known as HER-2/neu, is used to support the hypothesis that breaking self-recognition offers a novel therapeutic pathway (Disis et al., 1998a, b; 1999) although that method is not commonly accepted by most immunologists. The erbB-2 molecule is a transmembrane receptor with a significant extracellular portion. Its extracellular domain is commonly believed to be structurally similar for both cancer cells and normal cells. Thus, the advantages it possesses over intracellular antigen candidates is minimized because of its susceptibility to down regulation of any specific immune response on the basis of self recognition.

Use of derivatives of bombesin, an amphibian protein, was an attempt to inhibit growth of tumor cells that respond to bombesin (Knight et al., 1997). Bogden and Moreau attempted to treat human cancer by administering analogs of a biologically active peptide to a patient. However, these attempts used molecules that did not differentiate normal from cancer cells.

The deglycosylated mucins described by Barratt et al., 1998 and Henderson et al., 1998 are another example of a class of cancer-associated antigens with epitopes detectable outside of the cell. Mucins are large secreted and/or transmembrane glycoproteins with greater than 50% of their molecular weight derived from O-linked carbohydrates attached to serine and theonine. Their cancer specificity depends on a greater degree of altered structure rather than on numerical over-expression. The loss or diminution of carbohydrate side chains emanating from a central core protein makes the Muc proteins more immunogenic. Finn et al. ascribes this immunogenity as a result of significant altered molecular folding made possible by a release from molecular rigidity conferred by the many projecting glycoside chains found in mucin molecules in non-cancerous cells. The alteration in folding creates neo-epitopes which help break immune self-recognition and also separately facilitates stimulation of a cellular immune response. Problems with the Muc antigens include insufficient diversity needed to provide wide enough antigenic coverage for many cancers, and their rapid cellular release rate as a consequence of Muc antigens being secreted proteins, as opposed to functional cell membrane proteins such as receptor molecules, receptor-like molecules, or cell adhesion molecules. The latter attribute makes Muc antigens less effective therapeutic and imaging targets.

Hudziak et al. (1998a, b) describes the therapeutic utility of monoclonal antibodies specific for the extracellular domain of the normal HER-2/neu receptor (also known as erbB-2). The basis of this therapeutic method is described as the inhibition of the cancer-proliferative function of the receptor caused by the binding of a specific monoclonal antibody to the outer domain of the receptor thereby preventing the binding of circulating epidermal growth factor and other ligands to the receptor. Decreased or absent growth factor stimulation results in cancer cell death through apoptosis. This method relies on higher expression of Her-2/neu on cancer cells as compared to normal cells. Therapy is dose dependent. Sufficient blocking antibody must be administered so as to block enough cancer cell HER-2/neu molecules required to affect cancer cell death without causing normal cell death or normal cell toxicity. Adequate therapeutic dosing is not possible for all patients who express HER-2/neu on the their tumor cells. Some cancer patients express adequate amounts of HER-2/neu; some express low amounts; and yet others express none. Consequently, this therapeutic method works marginally, or not at all for most patients. Occasionally, when patient circumstances are appropriate, this method is capable of affecting total cancer remission. This limited result illustrates the basic soundness of a therapeutic method provided that a large repertoire of cancer-specific or cancer-associated functional targets were made available. However, more and better cancer-specific and cancer-associated antigens are needed to make these approaches clinically useful.

A method of preparing phosphorylated tumor specific peptides was reported by Calenoff (1998).

There are suggestions of expression of cancer-specific or cancer-associated molecules, as well as over-expression or under-expression of the molecules in or on cancer cells. For example, many receptor-like adhesion proteins found on the surface of cells have been described. Some of these adhesion proteins are reported to facilitate tumor migration and invasion (Zheng et al., 1999; Rabinovitz et al., 1995; Friedl et al., 1998) or metastatic spread (Romanov et al., 1999). Others are reported to facilitate essential functioning for both cancer cells and tissues and for normal cells and tissues (Ekblom et al, 1998; Fleischmajer et al., 1998; Bonkoff, 1998; Fujiwara et al., 1998; Lohi, 1998). Blocking certain functions facilitated by receptor-like adhesion molecules is suggested to provide new therapeutic modalities for eradicating or controlling cancer (Ruoslahti et al., 1997). Although various adhesion molecule isotypes are reported to be over-expressed (Damiano et al., 1999; Liapis et al., 1996; Begum et al., 1995; Katsura et al., 1998) or underexpressed (Furakawa et al., 1994; Damjanovich et al., 1997; Luguki et al., 1999) on cancer cells as compared to normal cells, none have been described which possess the cancer-specific or highly cancer-associated structural modifications of the present invention.

SUMMARY OF THE INVENTION

The invention relates to general methods and compositions that provide cancer-specific or highly cancer associated antigens useful for cancer diagnosis and treatment. An aspect of the invention is algorithms for determining, selecting and/or constructing synthetic peptides that are candidates for producing a cancer-specific or cancer-associated immune response useful in the diagnosis and treatment of cancer.

The invention also relates peptides selected by the methods of the present invention. The peptides are preferably small, e.g. from 3 to about 1000 amino acids in length, and are centered around amino acids that are generally glycosylated in non-cancerous cells, and are on the cell surface, but are not glycosylated in cancer cells. More preferred lengths of the peptides are from 3–7 amino acids or 3–10, or 5–10, although peptides up to about 25 or to 1000 amino acids in length, are also within the scope of the invention. The peptides are also hydrophilic. The peptides or fragments thereof include any variation in the amino acid sequence, whether by conservative amino acid substitution, deletion, or other processes, provided that the polypeptides are in accord with the criteria of the present invention. More specifically, more than one peptide, the sequences of which are in accord with the criteria of the present invention, are preferably present to enhance the discriminatory power of the immunoassays and therapies disclosed herein. That is, a plurality of antigenic peptides forms an array (or repertoire) of molecules suitable for diagnosis and treatment of cancer.

A peptide of the present invention contains both unmodified and modified amino acids. It is recognized that the conversion of a normal to a cancerous cell type likely involves many steps. At some point, a cell (more precisely, a group of cells—for example, a tumor) becomes distinguishable as a "cancer cell". If at that point, an amino acid differs in its state from that in non-cancerous cells, it is defined herein as "modified." Not all the cells in a cancerous tissue necessarily have the modification. For purposes of the present invention, it suffices that the modification allows some cancer cells to be distinguished from normal cells by detection of the modification or modifications.

On the external domain of proteins of cells with normal growth patterns, asparagine is the most frequent site of glycosylation, but in cancer cells the peptides of the present invention are missing a glycosidic complex altogether. The absence of the glycosidic complex is expected to confer a cancer-specific or highly cancer-associated immunogenicity to the altered peptide region. Deglycosylation is expected to remove steric hindrance present in non-cancerous cells, to phosphorylation or other modifications of the neighboring amino acids. Removal of steric hindrance allows available phosphorylases to add phosphate groups to amino acids usually under the glycosidic umbrella. Addition of phosphate groups facilitated by deglycosylation provides an additional cancer-specific or cancer-associated molecular structure to be detected.

The immunogenic peptides of the present invention may include one or more of the constituent amino acids that are chemically modified, either in the natural state of the cancer cells, or synthetic, and the chemical modification confers upon the peptide a cancer-specific or highly cancer-associated immunogenicity or structured uniqueness that is different from, and may be independent of, the specificity or association related to the altered (deglycosylated) glycosylation sites.

Following the steps outlined in Table 1, peptides suitable for the practice of the invention result in peptides with the formulas shown in Table 2.

TABLE 1

Steps in Obtaining Cancer Specific of Cancer-Associated Antigenic Peptides

Step 1:

obtain amino acid sequence of the extracellular domain of a candidate molecule e.g. a receptor or receptor-like molecule.

Step 2:

map hydrophilic regions of the domain by analyzing the amino acid sequence of the domain of step 1 employing the rolling sum analysis of 7 consecutive residues.

Step 3:

identify the hydrophilic regions of step 2 that are glycosylated in non-cancerous (normal) cells, but are deglycosylated in cancer cells. The deglycosylated regions of the peptide are candidates for being cancer-specific or cancer associated peptide antigens.

Step 4:

look for amino acids to either side of the deglycosylated amino acids identified in step 3 that are susceptible to alteration in the absence of steric hinderance by glycoside chains.

Step 5:

synthesize candidate peptides that fit the criteria obtained in steps 3 or 4 and label the peptides at one end e.g. with biotin.
use synthesized peptides as source antigens in immunoassays used to measure peptide-specific antibody in biological fluids (i.e. serum)

TABLE 1-continued

Steps in Obtaining Cancer Specific of Cancer-Associated Antigenic Peptides from cancer patients and biological fluids from control subjects. Peptides which specifically complex with antibody in cancer patient fluids but not in control fluids are cancer-specific antigens. Peptides which complex with antibodies in cancer patient fluids more frequently than they complex with antibodies from control fluids from (non cancerous patient, or at least not known to be cancer patients) are designated cancer-associated antigens. Peptides which complex with antibody in both cancer patient fluids and also control fluids, or with neither, are neither cancer-specific nor cancer-associated.

The invention is generally directed to immunogenic peptides which include a sequence of three or more amino acids, possess a net hydrophilic character, and contain at least one amino acid that is glycosylated in normal cells (generally an asparagine residue) but deglycosylated in cancer cells. As can be seen for the general forms in Table 2, the deglycosylated amino acid is located no further than:

1. 3 unmodified amino acids away from a fourth unmodified amino acid on either side of the deglycosylated amino acid;
2. 3 amino acids away from the most distal modified amino acid found on either side of the deglycosylated amino acid, where distal refers to a location from a deglycosylated amino acid;
3. 6 amino acids away from another deglycosylated amino acid (if there are no modified amino acids in between the two adjacent deglycosylated amino acids).

Arrays include differentiating pluralities of peptides of the present invention, to diagnose cancer.

An aspect of the invention is immunoassays employing immunogenic peptides to measure specific peptide-reactive antibodies in biological fluids, more specifically: an aspect of the invention is monoclonal antibodies and antibody-like molecules such as Fab2 and FAb fragments, known to those skilled in the art, and recombinant proteins thereof, which are specifically reactive with the immunogenic peptides of the present invention. Immunoassays employing these antibodies or antibody-like molecules of the present invention are used to measure in biological fluids, molecules containing altered peptide regions which correspond in vivo to the immunogenic peptides of the present invention.

Cancer imaging reagents are developed using labeled molecules of the present invention including antibodies or antibody-like molecules, directed toward cancer specific or cancer-associated peptides of the present invention. Suitable labels include radioisotopes, a paramagnetic label, and a water density label. The labels complexed with the antibodies or antibody-like molecules target cancer cells and tissues and respond to image detectors to identify the location of the cancer.

A therapeutic vaccine containing one or more immunogenic peptides of the present invention, and prepared by methods known to those skilled in vaccine development, is an aspect of the invention. Adjuvent/peptide conjugates including the immunogenic peptides coupled to molecules which facilitate enhanced immunogenicity, are used to stimulate the host immune system to facilitate the killing of cancer cells and thereafter maintain immune surveillance in case of cancer recurrence.

Vaccines created by recombinant techniques containing immunogenic peptides together with adjuvant molecular sequences which promote increased immunogenicity of the immunogenic peptides to stimulate the host immune system to facilitate the killing of cancer cells and thereafter maintain immune surveillance in case of cancer recurrence, are also within the scope of the invention.

Definitions

The term "antigen presenting cell" (APC) includes "professional antigen presenting cells" that constitutively express MHC class II molecules (e.g., B lymphocytes, monocytes, dendritic cells, Langerhans cells, and activated T cells in humans) as well as other antigen presenting cells that are capable of presenting antigen to T cells. APCs can express the appropriate combination of MHC molecules and costimulatory and/or adhesion molecules known in the art to be sufficient for presentation of antigen to T cells or can be induced or engineered to express such molecules.

As used herein, the term "immune response" includes T cell mediated and/or B cell mediated immune responses that are influenced by modulation of T cell costimulation. Exemplary immune responses include T cell responses, e.g., proliferation, cytokine production, and cellular cytotoxicity. In addition, the term "immune response" includes immune responses that are indirectly effected by T cell activation, e.g., antibody production (humoral responses) and activation of cytokine responsive cells, e.g., macrophages.

"Unmodified amino acids" are those found in the non-cancerous state—that is, as the amino acids exist in normal cells i.e. non-cancerous cells. Modified amino acids are those that exist in altered states in cancerous cells.

The term "markers," as used herein, includes any molecule which is detectable in a biological sample and indicates the presence of another molecule of interest. Some markers are antigenic. Markers are useful because their presence is associated with a disease or condition of interest. Markers of interest herein are those whose presence is associated with cancer.

The single letter code for amino acids, well known to those of skill in the art, is used herein.

BRIEF DESCRIPTION OF THE DRAWINGS

FIG. 1 presents the amino acid sequence (SEQ ID NO: 67) of the human epidermal growth factor receptor (EGFR); larger letters depict extracellular portions of human epidermal growth factor receptor (EGFR); the bold N denotes normally glycosylated asparagine residues on the EGFR extracellular portions; underlined amino acid sequences= hydrophilic peptide regions on extracellular portion of EGFR.

FIG. 2 presents amino acid sequence (portions of SEQ ID NO: 67) position numbers that indicate regions of cancer-specific/highly cancer-associated immunogenic peptides from the sequence shown in FIG. 1; N depicts deglycosylated asparagine in cancer-specific or highly cancer-associated immunogenic peptide regions; an underlined S, T or Y respectively depicts serine, threonine, and tyrosine amino acids which can become aberrantly phosphorylated because absent polysaccharide complexes emanating from the highlighted asparagines no longer sterically prevent various phosphorylases from approaching phosphorylate-able amino acids and attaching a phosphate group; the addition of a phosphate group creates a novel immunogenic peptide region centered by the phosphorylated amino acid(s) as well as the deglycosylated asparagine(s).

FIG. 3(a) graphically indicates screening results using the EGFR peptide (portion of SEQ ID NO: 67) rNvs; the x-axis shows results for 2 groups of serum samples:
 a. from patients with squamous cell carcinoma (dark circles);
 b. samples from patients not known to have any cancer (open circles);

Figure 7:
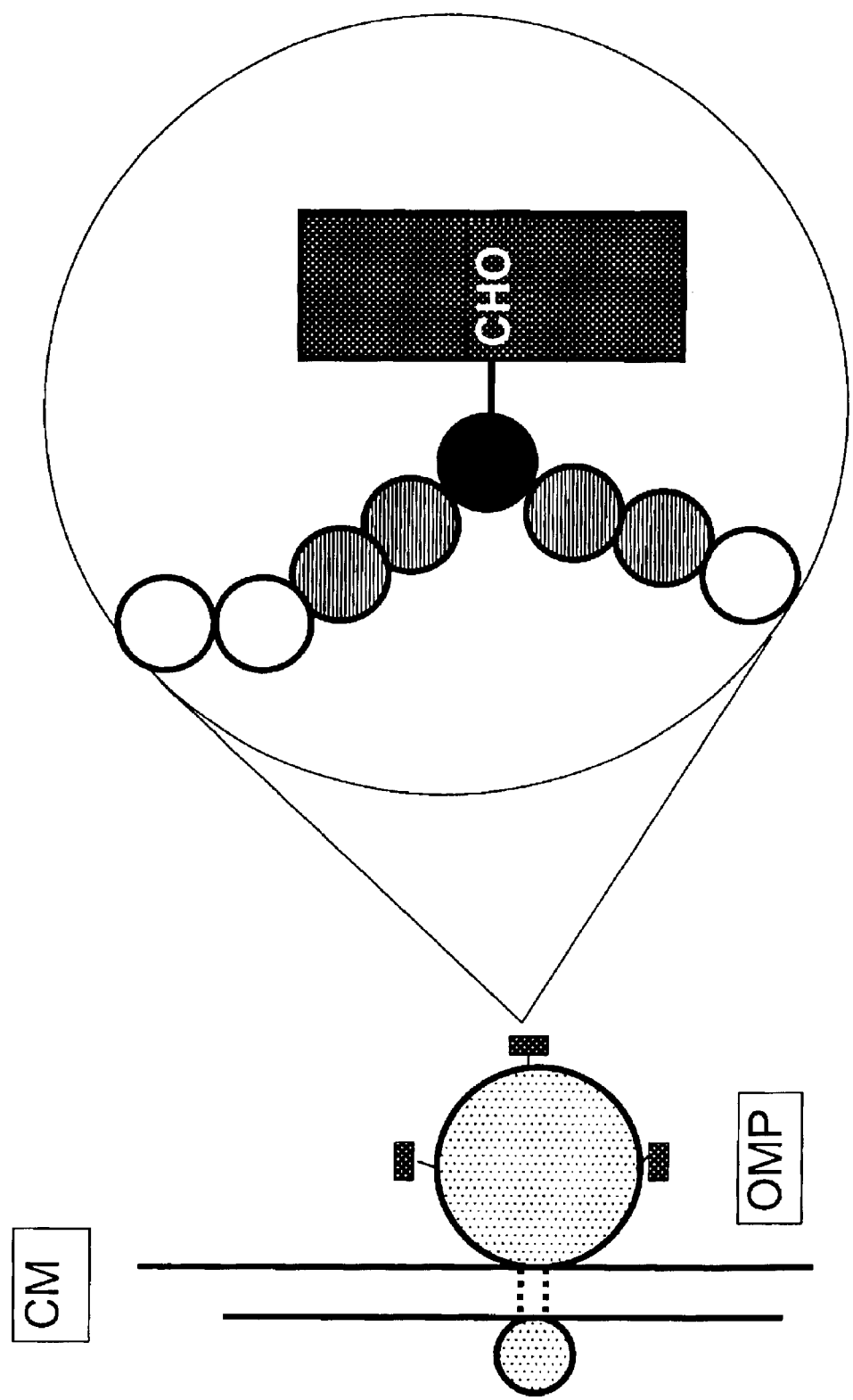

a dotted line shows the control (non-cancerous) population mean background+2.5 standard deviations antibody levels (serum IgG) shown on the y-axis were below the mean background+2.5 standard deviations of the mean (+2.5 SD) for all samples from persons not known to have cancer, whereas 2 of 45 of the samples from persons with squamous cell carcinoma, had antibody levels above the same mean+ 2.5 SD; this indicates that this peptide region of the epidermal growth factor receptor erbB-1, in altered form, likely serves as a cancer-specific immunogen or target.

FIG. 3(b) graphically indicates screening results using the EGFR peptide (portion of SEQ ID NO: 67) rNvSrgr; the x-axis shows results for 2 groups of serum samples:
  a. samples from patients with squamous cell carcinoma (dark circles);
  b. samples from patients not known to have any cancer (open circles);

antibody levels (serum IgG) shown on the y-axis) were below the mean background+2.5 SD for the serum samples from persons not known to have any cancer, whereas 3 of 45 serum antibody levels were above the same mean+2.5 SD for the serum samples for persons with squamous cell carcinoma; although the peptide antigen used to elicit these results is structurally related to the peptide (portion of SEQ ID NO: 67) rNvsr, the serum antibody levels elicited for the peptide (portion of SEQ ID NO: 67) rNvSrgr are much higher thus indicating that adding an aberrantly phosphorylated extension offers a neoantigen which complexes with specific serum antibody in excess to that afforded by the (portion of SEQ ID NO: 67) rNvsr peptide alone; this, too, indicates that this peptide region of the epidermal growth factor receptor erbB-1, in a second altered form, likely serves as a cancer-specific immunogen or target.

FIG. 4 graphically indicates screening results using the TROP1 peptide with the amino acid sequence (SEQ ID NO: 68) aemNgSk; the x-axis shows 2 groups of results:
  a. serum samples from persons with squamous cell cancer (dark circles); and
  b. serum samples from persons not known to have cancer (open circles);

the y-axis shows IgG antibody levels; 6 of 45 sera from cancer patients were above the mean background level from the controls+2.5 SD, whereas only one serum from the control population was above that level; this indicates that this peptide region of the TROP1 cell surface molecule in altered form, likely serves as a highly cancer-associated immunogen or target; the single positive result within the control population may also be indicative of silent (clinically undetectable) cancer presence in the affected subject.

FIG. 5 graphically illustrates serum antibody levels obtained with a plurality of 4 biotinylated peptides used as test antigens; the x-axis shows 2 groups:
  a. samples from persons with squamous cell cancer (dark circles);
  b. samples from persons not known to have cancer (open circles);

the y-axis shows IgG antibody levels; 11 of 45 sera from cancer patients were above the control mean background level+2.5 SD, whereas only one serum from the control population was above that level; this graph illustrates the positive summative effect of using a sufficiently large number of non-homologous synthetic peptides corresponding to the humorally antigenic peptide regions of cancer cell receptors and/or receptor-like molecules; by having enough suitable antigenic peptides in the antigen mix of the described immunoassay method, a point is reached where enough antigenic peptides are available to provide the immunoassay with a sensitivity approaching 100 percent while maintaining high specificity.

FIG. 6 graphically illustrates serum antibody levels obtained with 9 biotinylated peptides used as test antigens; the x-axis shows 7 groups:
  a. samples from persons with Stage I prostate cancer (dark circles);
  b. samples from persons with Stage II prostate cancer (open circles);
  c. samples from persons with Stage m prostate cancer (dark squares);
  d. samples from persons with Stage IV prostate cancer (open squares);
  e. samples from persons with benign prostatic hypertrophy (BPH), a non-malignant enlargement of the prostate (diamonds with crosses inside);
  f. samples from men not known to have cancer or BPH (open diamonds);
  g. samples from women not known to have cancer (dark triangles).

The y-axis shows IgG antibody levels; 4 of 7 sera (57%) from Stage I prostate cancer patients were above the mean background level+2.5SD; 3 of 7 sera (43%) from Stage II prostate cancer patients were above that level; 2 of 3 sera (67%) from Stage III prostate cancer patients were above that level; and 0 of 1 sera (0%) from Stage IV prostate cancer patients were above that level; whereas, only one serum (3.6%) from the BPH population and none of the normal males or females were above the threshold level; this graph also illustrates the positive summative effect of using a sufficiently large number of non-homologous synthetic peptides corresponding to the humorally antigenic peptide regions of cancer cell receptors and/or receptor-like molecules.

FIG. 7 is a diagram showing a glycosylated (CHO) amino acid (dark circle) in a peptide (chain of circles) in a non-cancerous cell and an outer membrane protein of a receptor—or receptor like molecule (OMP) with a transmembrane region (dashed line through a cell membrane (CM)) attached to an inner cell portion (small dotted circle).

Figure 8:
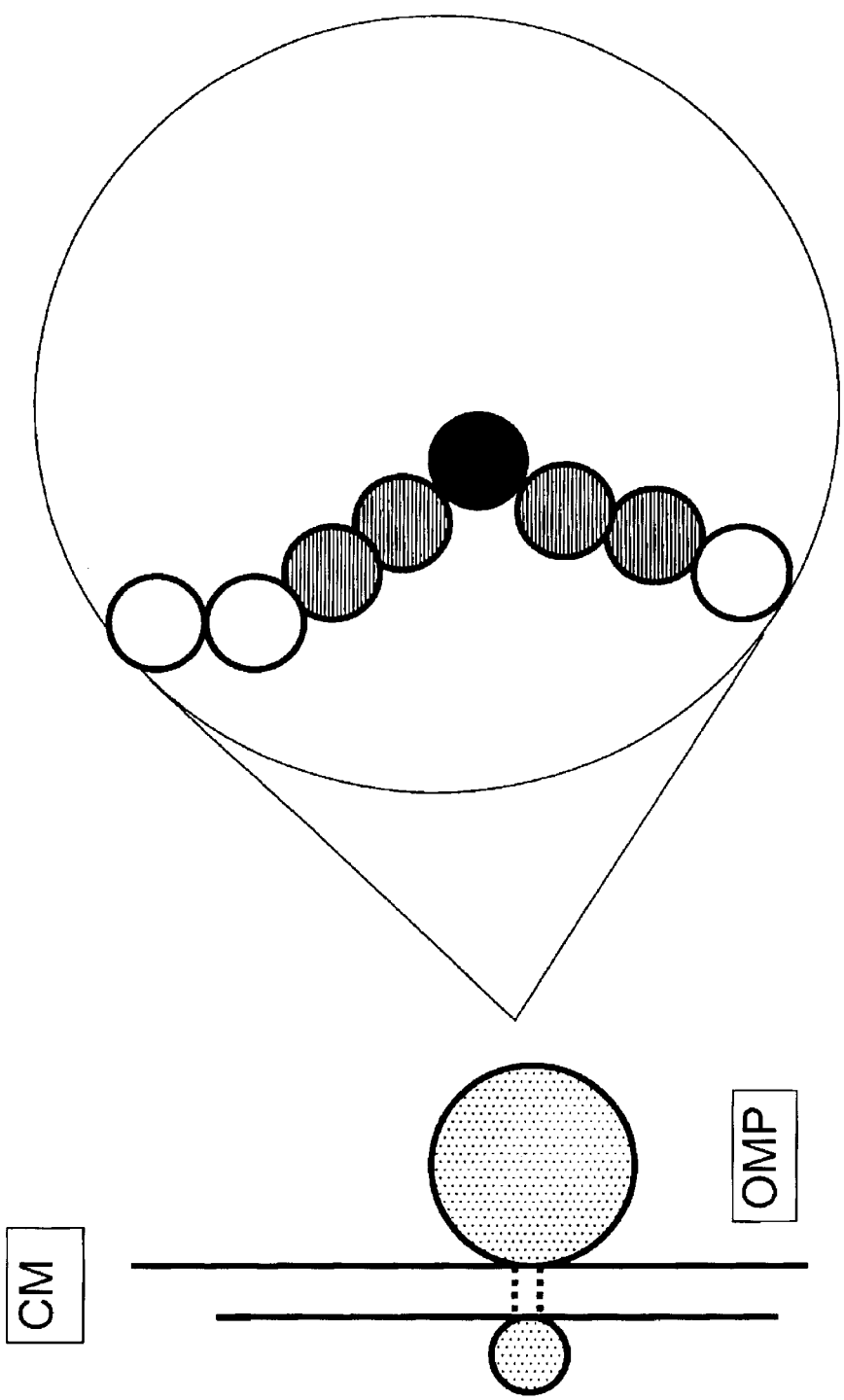

FIG. 8 is a diagram of the same structure as in FIG. 7 with the exception that the glycosylated amino acid in FIG. 7 (dark circle) is now deglycosylated, as in a cancerous cell.

Figure 9:
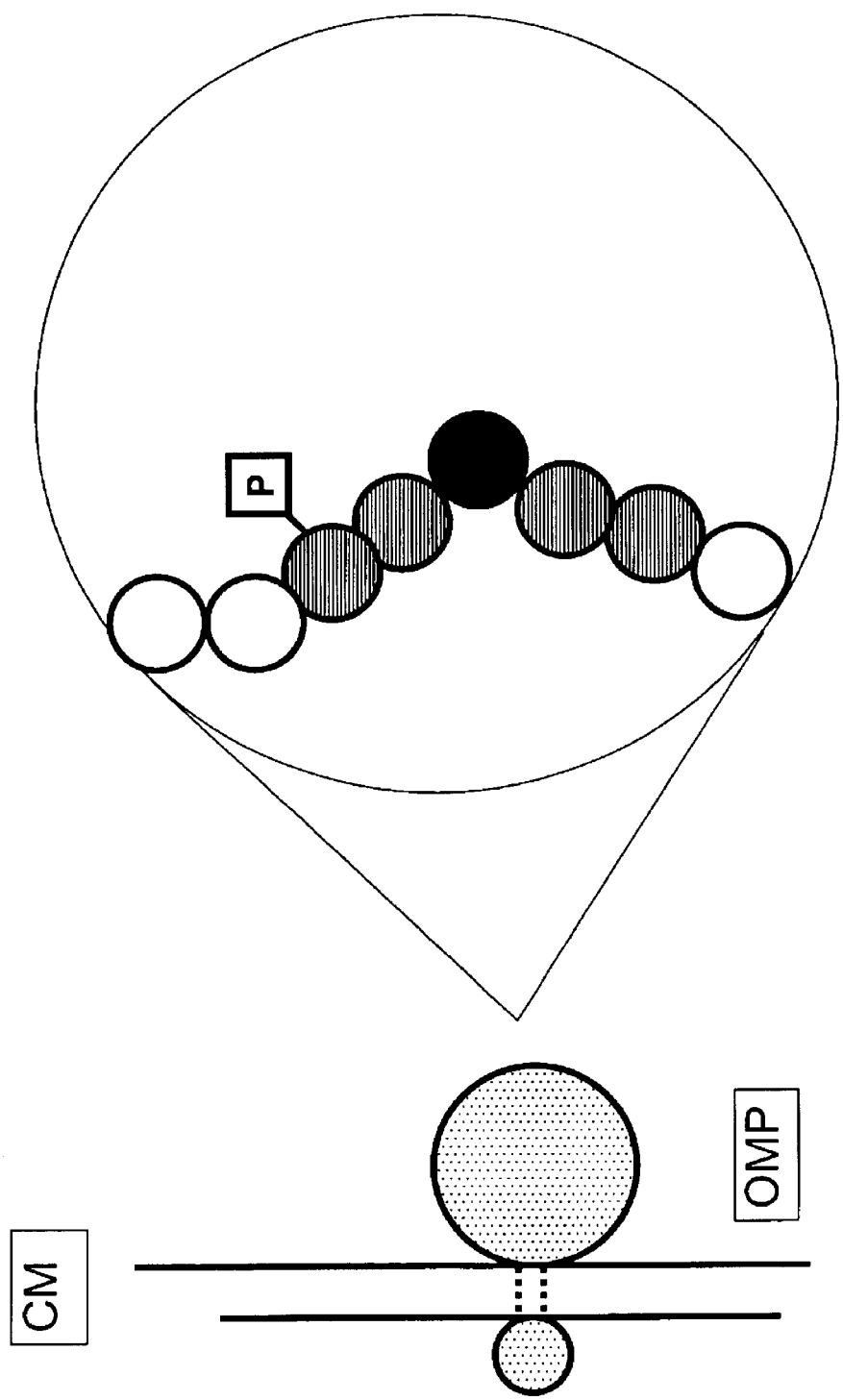

FIG. 9 is a diagram of the same of structure as in FIG. 8 except that one of the amino acids (shaded circles) in the peptide is phosphorylated (P), another modification in a cancer cell in addition to the deglycosylation shown in FIG. 8.

DESCRIPTION OF THE INVENTION

The invention relates to methods and compositions for obtaining cancer specific or cancer associated antigens (generally antigenic peptides) for use in diagnosis and treatment of cancer. An aspect of the invention is algorithms for determining, selecting and/or constructing antigens that are suitable for use in diagnostic tests for cancer, for producing cancer-specific or cancer-associated antibodies for use in diagnosis or treatment of cancer, and for producing immunogenic constructs for treatment of cancer. Aspects of the invention include a large repertoire (array) of cancer-specific and cancer-associated peptide antigens located on the surface of externally expressed cellular receptors or receptor-like molecules.

An algorithm for a peptide of the present invention directs among other things, that in the amino acid sequence, no more than 3 unmodified amino acids are located on either side of a modified amino acid (see Tables 1 and 2). Amino acid modification may include phosphorylation, conjugation of oxidized radicals (Tsimikas et al., 1999; Brame et al., 1999), and/or conjugation of glycosides(Shamsi et al., 1998) which differ from the glycosides which are normally attached to the peptide.

The antigens of the present invention generally have the following attributes and characteristics:

a. the antigens possess cancer-specific or cancer-associated alterations which confer antigenic and/or structural specificity upon the extracellular domains of commonly expressed receptor or receptor-like molecules;

b. the receptors and receptor-like molecules are potentially expressed by all cancer types thereby providing broad-based antigenic diversity and significant quantitative expression for most cancers;

c. the receptors and receptor-like molecules can serve as cell surface cancer-specific or cancer-associated antigens or as cell surface cancer markers;

d. the receptors and receptor-like molecules are found as early as Stage I as well as in Stages II, III, and IV of cancer progression;

f. because the receptor and receptor-like repertoire is significantly large, diminished expression among different cancers of some receptor or receptor-like molecules of the array is compensated by the standard expression or over-expression of other receptors or receptor-like molecules of the repertoire thereby providing sufficient antigenic and/or marker coverage. This varying molecular expression allows diagnostic discrimination of individual cancer types;

g. because the receptor and receptor-like repertoire is significantly large, enough receptor or receptor-like molecules are available which either remain affixed to the outer surface of cancer cells thereby serving as ideal antigenic or marker targets for diagnosis or therapy, or are predictably released into the peripheral circulation or biological fluids which bath the cancer cells thereby serving as shed cancer antigens to be measured for diagnostic purposes.

The antigen repertoire of this invention is different from the antigens reported by others in the following ways:

a. the MAGE antigens of Boon (1994) expressed in cancer cells are not structurally unique compared to MAGE concomitantly expressed in normal cells. MAGE antigens are intracellularly expressed and therefore require cancer cell damage or fragmentation for reliable extracellular expression;

b. the antigens described by Cheever (1997) possess cancer-specific structural alterations but are intracellular, or are over-expressed on the outer surface of cancer cells, but lack cancer-specific structural alterations which would confer immunogenic and/or marker specificity;

c. the Muc antigens described by Finn (1998 a, b) possess cancer- associated structural specificity that confers antigenic and/or marker specificity but are excreted and thereby poorly retained on the cancer cell surface. The structural alterations of Muc antigens are different from the alterations described for the antigens of the present invention. The antigenic/marker sites of peptides for this invention are small and are therefore less affected by a twisting-type of conformational change but rely more on peptide denuding and upon the modification of amino acids which are normally hidden by attached glycosides. The Muc antigen repertoire is numerically insufficient to provide across the board coverage for adenocarcinomas, which express Muc antigens;

d. the antigenic site employed in the method of Hudziak (1998 a,b) to target the HER-2/neu epidermal growth factor receptor is described as being structurally similar to HER-2/neu expressed by non-cancerous cells.

TABLE 2

Examples of formulas for suitable candidate cancer antigenic peptides (where u = unmodified amino acid; N = deglycosylated amino acid; $\underline{M}$ = modified amino acid and [ ]n symbolizes n number of repeats of a basic unit in brackets) are:

uNu
uNuu
Nuuu
uNuuu
uuNuu
uuNuuu
uuuNuuu
uNu$\underline{M}$uuu
uuNu$\underline{M}$uuu
uuuNu$\underline{M}$uuu
uuuN$\underline{MM}$uuu
uuuNu$\underline{MM}$uuu
uuuN$\underline{MMM}$uuu
uNuu$\underline{M}$uu
uNuu$\underline{M}$uuu
uuNuu$\underline{M}$uuu
uuuNuu$\underline{M}$uuu
uuNuu$\underline{M}$uuNuu
uuuNuu$\underline{M}$uuNuuu
uuu$\underline{M}$uuNuu$\underline{M}$uuu
[uuNuuN]n
[uuuNuuuN]n
[uuuNuuuuN]n
[uuuNuuuuuN]n
[uuuNuuuuuN]n
[uuuNuuuuuuN]n
[uuuNuuuuuuNu]n
[uuuNuuuuuuNuu]n
[uuuNuuuuuuNuuu]n
[uu$\underline{M}$uuN]n

TABLE 3

Comparison of Peptides Present in Serum From Cancer Patients to Peptide Sequences Cancer Tissue (SEQ ID NOS 1–66, respectively, in order of appearance)

| Cell Surface Proteins (CSP) | Tested CSP Peptides | Prostate Cancer Serum Test Result | Presence of Absence of CSP in Prostate Cancer |
|---|---|---|---|
| E-Cadherin | vkNst (SEQ ID NO: 1) | + | + |
| N-Cadherin | dkNls (SEQ ID NO: 2) | + | + |
| CD9 | nnNNss (SEQ ID NO: 3) | − | − |
| CD38 | dkNst (SEQ ID NO: 4) | − | − |
| CD40 | gtNkt (SEQ ID NO: 5) | + | + |
| CD44 | drNgt (SEQ ID NO: 6) | + | + |
|  | NhSeg (SEQ ID NO: 7) | + |  |
|  | spNhs (SEQ ID NO: 8) | − |  |
| CD46 | drNht (SEQ ID NO: 9) | − | − |
| CD53 | sdNst (SEQ ID NO: 10) | − | − |
| CD55 | fCNrs (SEQ ID NO: 11) | − | − |
| CD63 | knNht (SEQ ID NO: 12) | − | − |
| CD66 | saNrs (SEQ ID NO: 13) | + | + |
|  | trNdt (SEQ ID NO: 14) | − |  |
|  | skNqs (SEQ ID NO: 15) | − |  |
| CD82 | pgNrt (SEQ ID NO: 16) | − | − |
| desmoglein 1 | tkNgt (SEQ ID NO: 17) | − | − |

TABLE 3-continued

Comparison of Peptides Present in Serum From Cancer Patients to Peptide Sequences Cancer Tissue (SEQ ID NOS 1–66, respectively, in order of appearance)

| Cell Surface Proteins (CSP) | Tested CSP Peptides | Prostate Cancer Serum Test Result | Presence of Absence of CSP in Prostate Cancer |
|---|---|---|---|
| desmoglein 2 | kiNat (SEQ ID NO: 18) | − | − |
| erbB-1 | daNkt (SEQ ID NO: 19) | + | + |
|  | perNrt (SEQ ID NO: 20) | − |  |
|  | crNvs (SEQ ID NO: 21) | − |  |
| erbB-2 | dtNrs (SEQ ID NO: 22) | + | + |
| erbB-3 | heNct (SEQ ID NO: 23) | − | + |
| erbB-4 | aeNct (SEQ ID NO: 24) | − | − |
|  | pdNct (SEQ ID NO: 25) | − |  |
| fgfr1 | esNrt (SEQ ID NO: 26) | − | + |
| fgfr2 | ekNgs (SEQ ID NO: 27) | − | + |
| fgfr4 | diNss (SEQ ID NO: 28) | − | − |
| hepatocyte gfr | vgNks (SEQ ID NO: 29) | − | + |
| pdgfr alpha | eeNns (SEQ ID NO: 30) | − | + |
| pdgfr beta | kdNrt (SEQ ID NO: 31) | − | − |
|  | trNvs (SEQ ID ND: 32) | − |  |
| ICAM 1 | hkNqt (SEQ ID NO: 33) | − | + |
| integrin alpha 1 | qrNit (SEQ ID NO: 34) | − | − |
|  | seNas (SEQ ID NO: 35) | − |  |
| integrin alpha 2 | drNhs (SEQ ID NO: 36) | − | − |
| integrin alpha 3 | meNkt (SEQ ID NO: 37) | + | + |
|  | leNht (SEQ ID NO: 38) | − |  |
|  | rmNit (SEQ ID NO: 39) | − |  |
| integrin alpha 5 | kaNts (SEQ ID NO: 40) | − | − |
|  | lrNes (SEQ ID NO: 41) | − |  |
| integrin alpha 6 | raNhs (SEQ ID NO: 42) | − | + |
| integrin alpha 9 | qkNqt (SEQ ID NO: 43) | − | − |
|  | kgNcs (SEQ ID NO: 44) | − |  |
| integrin alpha (v) | qdNkt (SEQ ID NO: 45) | + | + |
|  | kaNtt (SEQ ID NO: 46) | − |  |
|  | teNqt (SEQ ID NO: 47) | − |  |
|  | ekNdt (SEQ ID NO: 48) | − |  |
| integrin beta I | nkNvt (SEQ ID NO: 49) | + | + |
|  | vtNrs (SEQ ID NO: 50) | − |  |
|  | kNvtNrs (SEQ ID NO: 51) | − |  |
|  | keNss (SEQ ID NO: 52) | − |  |
|  | eqNct (SEQ ID NO: 53) | − |  |
| integrin beta 3 | skNfs (SEQ ID NO: 54) | − | − |
| integrin beta 5 | rcNgs (SEQ ID NO: 55) | − | − |
|  | pdNqt (SEQ ID NO: 56) | − |  |
| integrin beta 6 | qkNss (SEQ ID NO: 57) | − | − |
|  | evNss (SEQ ID NO: 58) | − |  |
| protein-tyrosine phosphatase PCP-2 | seNdt (SEQ ID NO: 59) | − | − |
| protein-tyrosine phosphatase kappa | keNdt (SEQ ID NO: 60) | − | − |
|  | ghNes (SEQ ID NO: 61) | − |  |
|  | gdNrt (SEQ ID NO: 62) | − |  |
| tgfr beta type II | deNit (SEQ ID NO: 63) | + | + |
|  | eyNts (SEQ ID NO: 64) | + |  |
| insulin-like gf receptor | pdNdt (SEQ ID NO: 65) | − | + |
|  | mNtt (SEQ ID NO: 66) | − |  |

Table 3 column 2 to the right is a compilation of cancer-modified peptide regions to be found on 41 receptors, receptor-like molecules, or adhesion molecules reported in the literature (CSP). This table illustrates the diversity of tissue and organ types which possess receptors, receptor-like molecules, or adhesion molecules able to present with cancer-specific or highly cancer-associated structural alterations.

Table 3 third column illustrates the positive or negative reactivity between peptides representing modified peptide regions of cancer cell surface protein molecules with antibodies in sera from prostate cancer patients. The presence or absence in prostate cancer cells of the 41 tested molecules is shown as + or − in column four. Table 3 illustrates that reactivity exists between most of the modified peptides of prostate cancer cell surface molecules but shows no reactivity with modified peptide regions of molecules not found in prostate cancer, thus illustrating the ability to serologically determine cancer type by having first mapped out the peptide antigen repertoire needed to identify each cancer. These results support feasibility of using the peptides of the present invention, in particular a plurality of peptides, for cancer diagnosis.

An aspect of the invention is monoclonal antibodies and antibody-like molecules such as Fab2 and FAb fragments, known to those skilled in the art, and recombinant proteins (Hussain et al., 1996).

A cancer imaging reagent is developed using molecules including labeled antibodies or antibody-like molecules directed to antigenic peptides of the present invention. Suitable labels include a radioisotopic label for the cancer imaging reagents which, upon binding to the cells that form a cancerous tumor, highlight the presence of the tumor when scanned with a nuclear medicine scanner (Goldenberg, 1993; 1999).

Another suitable label is a paramagnetic label which, upon binding to the cells of a cancerous tumor, highlights the presence of the tumor when scanned with a nuclear magnetic resonance (NMR) scanner (To et al., 1992).

Another suitable label comprises a water density label which, upon binding to the cells of a cancerous tumor, highlights the presence of the tumor when scanned with a CAT scanner.

Cancer therapeutic reagents developed using the molecules including antibodies or antibody-like molecules directed to the peptides of the present invention, have at least one of the following characteristics: they (1) bind to a cancer cell and promote lysis of that cell; (2) bind to and block the function of a receptor or receptor-like molecule on a cancer cell, thereby promoting a reduction or cessation of cancer cell growth or promoting cancer cell death; and (3) carry a radioisotope or a toxin which upon binding to a cancer cell damages or promotes cancer cell death (Goldenberg, 1993).

Examples of cancer therapeutic methods which can be formulated using a suitable cancer antigens/markers array are (see Materials and Methods for details and citations):

a. passive immunization using constructs such as engineered antigen presenting cells and production of antigen presenting dendritic cells able to stimulate the host immune system to recognize and kill cancer cells;

b. active immunization using cancer vaccines including recombinant fusion proteins, vaccine compositions containing adjuvants, vaccine compositions containing nucleic acid molecules, recombinant microorganisms which express cancer antigens, antigen/antibody conjugates wherein the antibody acts as a delivery vehicle for targeting the antigen onto antigen presenting cells, and heat shock protein/antigen complexes;

c. cell lytic therapeutic antibodies, cell adhesion blocking antibodies, and growth factor receptor blocking antibodies.

Therapeutic methods using the non-phosphorylated peptide antigens of the present invention, either their amino acid sequences or the corresponding nucleic acid sequences that encode the peptides include the following:

a. passive immunization using constructs such as engineered antigen presenting cells and production of antigen presenting dendritic cells able to stimulate the host immune system to recognize and kill cancer cells;

b. active immunization using cancer vaccines including recombinant fusion proteins, vaccine compositions containing adjuvants, vaccine compositions containing nucleic acid molecules, recombinant microorganisms which express cancer antigens, antigen/antibody conjugates wherein the antibody acts as a delivery vehicle for targeting the antigen onto antigen presenting cells, and heat shock protein/antigen complexes.

Criteria for an antigen array suitable for passive immunotherapy specific for cancerous cells include the following:

1. each type of cancer possesses antigens such as protein, peptide, carbohydrate, or lipid molecules which are structurally unique as compared to non-cancerous cells and are also immunogenic;
2. the cancer antigens are located on the cell surface so they are sufficiently accessible for targeting T cells;
3. the cancer antigens are present at the earliest stages of cancer progression as well as during later stages;
4. each cancer cell must have on its surface a sufficient number of specific antigens to serve as an adequate target for an effective cellular-mediated immune response;
5. the cancer antigens are retained on the surface of the cancer cells for a time sufficient for the therapeutic T cells to find their target and also to retain the bound T cells for a time sufficient to affect cancer cell death.

Criteria, for an antigen array suitable for developing effective constructs for active immunotherapy include the following:

1. each cancer type possesses antigens such as protein, peptide, carbohydrate, or lipid molecules which are structurally unique as compared to non-cancerous cells and are also immunogenic;
2. the cancer antigens are located on the cell surface to be sufficiently accessible and thus more easily recognized by the host immune system;
3. the cancer antigens are present at the earliest stages of cancer progression as well as during later stages;
4. each cancer cell has on its surface a sufficient number of specific antigens that serve as an adequate target for a humoral and/or cellular-mediated immune response;
5. the cancer antigens are retained on the surface of the cancer cells for a time sufficient for the therapeutic effector cells, and antibodies elicited by the immunostimulatory constructs to find their target and also to retain the effector cells and antibodies for a time sufficient to affect cancer cell death.

Criteria for a marker array including an antigen suitable for developing cell-lytic therapeutic antibodies include the following:

1. each cancer type possesses markers such as protein, peptide, carbohydrate, or lipid molecules which are structurally unique as compared to non-cancerous cells;
2. the cancer markers are available in sufficient numbers on the surface of cancer cells to provide an adequate therapeutic target at the earliest stages of cancer progression as well as during later stages;
3. the cancer markers are retained on the surface of the cancer cells for a time sufficient for the therapeutic antibodies to find their target and also to retain the bound antibody for a time sufficient to affect cancer cell death.

Criteria for a marker array suitable for developing growth factor receptor blocking antibodies include:

1. each cancer type possesses markers such as protein, peptide, carbohydrate, or lipid molecules which are structurally unique as compared to non-cancerous cells;
2. the cancer markers are available in sufficient numbers on the surface of cancer cells to provide an adequate therapeutic target at the earliest stages of cancer progression as well as at later stages;
3. the cancer markers are retained on the surface of the cancer cells for a time sufficient for the growth factor receptor blocking antibodies to find their target and also to retain the bound antibody for a time sufficient to affect cancer cell death;

Criteria for a marker array suitable for developing cell surface adhesion blocking antibodies include:

1. each cancer type possesses receptor-like adhesion molecules which are structurally unique as compared to non-cancerous cells;
2. the adhesion molecules are available in sufficient numbers on the surface of cancer cells to provide an adequate therapeutic target at the earliest stages of cancer progression as well as at later stages;
3. the cancer markers are retained on the surface of the cancer cells for a time sufficient for adhesion blocking antibodies to find their target and also to retain the bound antibody for a time sufficient to prevent cancer cell attachment, migration, de-differentiation or other function essential for cancer cell survival or metastasis.

Those of skill in the art recognize that identification of Stage I cancer generally provides a 90 percent or greater cure rate through the use of currently available cancer therapies (DeVita et al., 1985). Therefore, diagnostic assays for early stage cancer are extremely important.

Examples of cancer diagnostic methods which can be formulated using a suitable cancer antigen/marker repertoire are: cancer-specific antibody assays, cancer-specific antigen assays, and in-vivo cancer imaging.

Criteria for an antigen array suitable for developing cancer-specific antibody assays include:

1. each cancer type possesses antigens such as protein, peptide, carbohydrate, or lipid molecules which are structurally unique as compared to non-cancerous cells and are also immunogenic;
2. the cancer antigens are located on the cell surface to be sufficiently accessible and thus more easily recognized by the host immune system;
3. enough cancer cells have on their surface a sufficient number of specific antigens to elicit an immune response capable of being measured at the earliest stages of cancer progression as well as at later stages and among most affected patients.

Criteria for a marker array suitable for developing cancer-specific antigen-capture immunoassays include the following:

1. each cancer type possesses markers such as protein, peptide, carbohydrate, or lipid molecules which are structurally unique as compared to non-cancerous cells;
2. the cancer markers are predictably secreted or otherwise released into the pericellular fluids to be reliably measured;
3. enough cancer cells shed enough specific marker from within a cancerous tumor to be reliably measured at the earliest stages of the tumor's progression and during later stages of most affected patients.

Criteria for a marker array suitable for developing cancer-specific imaging reagents include the following:

1. each cancer type possesses markers such as protein, peptide, carbohydrate, or lipid molecules which are structurally unique as compared to non-cancerous cells;

2. the cancer markers are available in sufficient numbers on the surface of cancer cells to provide an adequate imaging target at the earliest stages of cancer progression as well as during later stages;

3. the cancer markers are retained on the surface of the cancer cells for a time sufficient for the imaging agents to find their target and also to retain the bound imaging agent for a time sufficient to record the presence and location of the cancer.

Possible Outcomes for Peptides Screened as Antigens in Serum Antibody Assays

1. A positive result indicating the presence of a peptide-specific antibody in cancer patient biological fluid samples, absent evidence of antibody in samples from subjects without cancer (FIG. 3) indicates the tested peptide is a cancer-specific peptide (immunogen).

2. A significantly higher positive prevalence of a peptide-specific antibody in cancer patient biological fluid samples as compared to samples from subjects without cancer (FIG. 4) indicates either that the tested peptide is cancer specific and that the few control positives have asymptomatic cancer or that the peptide serves as a highly cancer-associated antigen.

3. No difference in positive antibody levels between cancer patients and subjects without cancer. Biotinylated peptides producing these results are neither cancer specific nor highly cancer-associated.

EXAMPLES

The following examples illustrate embodiments of the invention.

Example 1

Use of the EGFR Peptide on Serum from Cancer Patients and Controls

Using immunoassay 2 (see Materials and Methods) the following results were obtained.

FIG. 3(a) graphically indicates screening results using the EGFR peptide (portion of SEQ ID NO: 67) rNvs; the x-axis shows results for 2 groups of serum samples:

a. from patients with squamous cell carcinoma;

b. samples from patients not known to have any cancer; antibody levels (serum IgG) were below the mean background plus 4 standard deviations of the mean (+2.5 SD) for all samples from persons not known to have cancer, whereas 2 of 45 of the samples from persons with squamous cell carcinoma, had antibody levels above the mean+4 SD.

FIG. 3(b) graphically indicates screening results using the EGFR peptide (portion of SEQ ID NO: 67) rNvSrgr; the x-axis shows results for 2 groups of serum samples:

a. samples from patients with squamous cell carcinoma;

b. samples from patients not known to have any cancer, antibody levels (serum IgG) were below the median background plus 2.5 SD for the serum samples from persons not known to have any cancer, whereas 3 of 45 serum levels were above the median+2.5 SD for the serum samples for persons with squamous cell carcinoma.

Example 2

Use of the TROP1 Peptide on Serum Samples from Cancer Patients Compared to Controls FIG. 4 graphically indicates screening results using the TROP1 peptide with the amino acid sequence (portion of SEQ ID NO: 68) emNgSk; the x-axis shows 2 groups of results:

a. serum samples from persons with squamous cell cancer; and b. serum samples from persons not known to have cancer; the y-axis shows IgG antibody levels; 6 of 45 serum from cancer patients were above the median background level+2.5 SD, whereas only one serum from the control population was above that level.

Materials and Methods

A Method for Selecting Cancer-Specific or Highly Cancer-Associated Immunogenic Peptides and/or Markers The identification and validation (or confirmation) of cancer-specific and cancer-associated antigenic peptide regions and/or marker peptide regions found on the extracellular domain of receptors or receptor-like molecules is performed through the use of a algorithms such as the following:.

First, the amino acid sequence of the extracellular domain of a receptor or receptor-like molecules is obtained. For example, the human epidermal growth factor receptor (EGFR), erbB-1, as illustrated in FIG. 1.

Second, the amino acid sequence is analyzed employing rolling sum analysis of 7 consecutive residues (Hopp et al., 1981; Parker et al., 1986; Fauchere et al., 1983; Taragu et al., 1990) in order to map out peptide regions which are hydrophilic and therefore apt to be expressed on the outer surface of the protein. For example, the hydrophilic regions of the EGFR outer domain are underlined in FIG. 1.

Third, hydrophilic peptide regions containing amino acids which are normally glycosylated are identified. These amino acids, illustrated by a bold capital letter N in FIG. 1, are apt to be totally (or partially) deglycosylated in cancer cells. The absence or truncation of the glycoside chain results in peptide structures which are structurally distinct for cancer cell proteins. The distinctly structured peptide regions can serve as a tumor-specific antigenic site if this alteration is not expressed in normal cells, or can serve as a cancer-associated antigen by cancer cells. The ability of a peptide to serve as an antigen depends on the host's immune system being able to process and recognize the peptide as an antigen. The processing and recognition of an antigen is dependent on individual MHC genotypes. If an altered peptide cannot serve as a cancer-specific or cancer-associated antigen, it may still be useful as a molecular marker of cancer on the basis of its cancer-specific or cancer-associated molecular alteration.

Fourth, the deglycosylated peptide regions are evaluated for the inclusive presence of amino acids that are susceptible to alteration in the absence of glycoside chains which normally would sterically restrict the contact of enzyme or other agents with the amino acids susceptible to molecular modification. The amino acid modification confers a second order alteration on the affected peptide which can result in a new and distinct peptide structure with specific antigenic and/or marker properties. Examples of such an amino acid modification include aberrant phosphorylation of serine, threonine, and tyrosine residues, malondialdehyde (MDA) modification of lysine residues, aberrant glycosylation of arginine residues, and the like.

Fifth, candidate peptides which fit the criteria of the cancer-modified peptide regions described in Steps 1 through 4 are synthesized and biotin labels are attached at either end of each peptide.

Sixth, employing the immunoassays disclosed herein, each biotinylated peptide is screened as an antigen against sera or other relevant biological fluids containing antibodies taken from one of the following groups: cancer patients, patients with benign lesions or inflammatory conditions, and healthy subjects. Peptides can also be screened using tumor-infiltrating lymphocytes or peripheral blood-born lymphocytes from cancer patients. Candidate peptides we consider cancer-specific or cancer-associated depend on whether they fit the following definitions.

Potentially useful peptides prepared in accord with steps 1–5 preferably possess the following attributes:

a. contain no more than 3 unmodified amino acids attached on either side of a deglycosylated amino acid or a modified amino acid. Peptides containing both deglycosylated amino acids and modified amino acids have no more than 2 unmodified amino acids between the deglycosylated amino acids and the modified amino acids. Peptides with more unmodified amino acids on either side of a deglycosylated amino acid become antigenically less differentiating for cancer as the respective unmodified amino acid numbers increase. The EGFR peptide (portion of SEQ ID NO: 67) danktg in FIG. 2 represents a peptide suitable for the practice of the invention, with a single deglycosylated amino acid at its central portion. The EGFR peptide (portion of SEQ ID NO: 67) daNkTglk in FIG. 2 represents a suitable peptide with both a modified amino acid and a deglycosylated amino acid in its central portion.

b. a plurality of deglycosylated amino acids and modified amino acids providing that the modified amino acids proximal to a deglycosylated amino acid are no further than the third amino acid position from the nearest deglycosylated amino acid and that 2 or more deglycosylated amino acids in a peptide are connected by no more than 6 unmodified amino acids.

Synthesis of Deglycosylated Peptides and Phosphorylated, Modified Forms

Methods of synthesis of peptides and their corresponding, encoding nucleic acid molecules are well know in the art and can be obtained commercially from U.S. companies such as the American peptide Company (Sunnyvale, Calif. 94086) and Commonwealth Biotechnologies, Inc. (Richmond, Va., 23235).

Immunoassay Method 1: Used to Detect Serum IgA, IgD, IgE, IgG, and IgM Antibodies Specific for Individual Peptide Antigens Materials Neutravidin coated microtiter plates manufactured as per Example 4.

Wash Buffer: 20 mM Tris-HCl+150 mM NaCl+0.05% Triton X405+0.2 mg/mL thimerosal, pH 7.4.

Biotinylated peptide solution containing 1.5 g/mL peptide in 20 mM Tris-HCl+600 mM NaCl+30 mg/mL polyethylene glycol 4000 (PEG-4000, Mallinckrodt Chemical H273-61)+ 0.05% Triton X405+0.2 mg/mL thimerosal, pH 7.4.

Anti-IgA/alkaline phosphatase (Kirkegaard and Perry 075–1001)+anti-IgG/alkaline phosphatase (Kirkegaard and Perry 075-1002) solution: 0.3 g/mL of each conjugate in solution containing 20 mM Tris-HCl+600 mM NaCl+30 mg/mL polyethylene glycol 4000 (PEG4000, Mallinckrodt Chemical H273-61)+0.05% Triton X405+0.2 mg/mL thimerosal, pH 7.4.

4-methylumbelliferyl phosphate (4-MUP) fluorescing substrate solution:

25.2 mg 4-MUP (Sigma M-8883)/mL solution containing 180 mM 2-amino-2-methyl-1-propanol+123 mM magnesium chloride, pH 9.5.

Fluorolite 1000 microtiter plate fluorometer (Dynatech) with excitation set at 365 nm and emission at 450 nm.

Procedure:

1) Adsorb neutravidin (NA) reactive antibodies and biotin reactive antibodies from serum samples by adding one neutravidin-conjugated paper disc to every 25 mL of serum and 1 biotin-conjugated paper disc to every 200 mL serum. Allow disc/serum mixture to incubate for 26 to 18 hours at room temperature, under gentle agitation.

2) Mix 75 mL of adsorbed serum together with 75 mL of peptide solution.

3) Vortex mixture and let incubate at room temperature for 40 minutes.

4) Aspirate well contents and wash microtiter wells of neutravidin plate (275 mL wash buffer/well)×6.

5) Add 100 mL biotinylated peptide/serum solution to corresponding well and incubate for 3.5 minutes.

6) Aspirate well contents and wash microtiter wells (275 mL wash buffer/well)×6.

7) Add 100 mL anti-IgA/alkaline phosphatase+anti-IgG/ alkaline phosphatase conjugate solution and incubate for 40 minutes.

8) Aspirate well contents and wash microtiter wells (275 mL wash buffer/well)×6.

9) Add 100 mL 4-MUP substrate solution.

10) Read derived fluorescence using microtiter plate fluorometer at 5, 10, 20, 30, and 60 minutes.

Immunoassay Method 2: Used to Detect Serum IgA, IgD, IgE, IgG, and IgM Antibodies Specific for Individual Peptide Antigens Materials:

NeutrAvidin$^a$ conjugated paper disc, 6 mm.

Serum diluent: 10 mM sodium phosphate, pH 7.20, with 150 MM sodium chloride, and 0.20 mg/mL sodium azide.

NeutrAvidin$^a$ coated white microtiter plate, stored in 10 mM Tris-HCl, pH 7.50, containing 600 mM sodium chloride and 0.2 mg/mL thimerosal.

Plate blocking solution: 10 mM sodium phosphate, pH 7.20, containing 150 mM sodium chloride, 100 mg/mL Triton X-405, and 0.2 mg/mL thimerosal.

Plate wash buffer: 20 mM Tris chloride, pH 7.4, containing 150 mM sodium chloride, 0.5 mg/mL Triton X-405 and 0.2 mg/mL thimerosal.

Peptide solution: 0.06 µg/mL peptide dissolved in 20 mM Tris chloride, pH 7.4, containing 600 mM sodium chloride, 30 mg/mL polyethylene glycol 4000, 1 mM ethylenediaminetetraacetic acid, 1 mM ethylene glycol-bis(§-aminoethyl ether)N,N,N',N'-tetraacetic acid, 0.5 mg/mL Triton X405 and 0.2 mg/mL thimerosal.

Control peptide solution: 0.013 µg/mL control peptide dissolved in 20 mM Tris chloride, pH 7.4, containing 600 mM sodium chloride, 30 mg/mL polyethylene glycol 4000, 1 mM ethylenediaminetetraacetic acid, 1 mM ethylene glycol-bis(§-aminoethyl ether)N,N,N',N'-tetraacetic acid, 0.5 mg/mL Triton X-405 and 0.2 mg/mL thimerosal.

Conjugate solution: 0.100 µg/mL alkaline phosphatase conjugated polyclonal goat anti human IgG dissolved in 20 mM Tris-HCl, pH 7.40, with 600 mM sodium chloride, 30.0 mg/mL PEG-4000, 3.0 mg/mL BSA, 0.5 mg/mL Triton X-405 and 0.20 mg/mL thimerosal.

Substrate solution: 25.2 µg/mL 4-methylumbelliferyl phosphate dissolved in 180 mM 2-amino-2-methyl-1-propanol, pH 9.50, containing 123 µM magnesium chloride.

Serum preparation:

1. Add 100 µL serum to 15 NeutrAvidin$^a$ coated paper discs in a suitably sized test tube.

2. Incubate with gentle mixing at ambient temperature for 16–20 hours.

3. Add 7.900 mL of serum diluent and mix gently for 30 minutes.

4. Vortex the tube gently to completely release the serum from the discs.
5. Remove the treated serum from the discs and transfer it to a suitable storage tube.
6. Store the treated serum at 4 EC.

Assay procedure:
1. Two days before assay, aspirate the storage solution from the NeutrAvidin$^a$ coated white microtiter plate and add 200 μL plate blocking solution to each well.
2. Cover the plate and incubate at ambient temperature for 16–20 hours.
3. One day before assay. wash the blocked plate three times with plate wash buffer, approximately 275 μL per well per wash. Aspirate the final wash and add 100 μL peptide solution or 100 μL control peptide solution to the appropriate wells of the plate.
4. Cover the plate and incubate with gentle mixing at ambient temperature for 16–20 hours.
5. Day of assay, wash the blocked plate three times with plate wash buffer, approximately 275 μL per well per wash. Aspirate the final wash and add 100 μL treated serum to the appropriate wells of the plate.
6. Cover the plate and incubate at 25 EC for 2 hours.
7. Wash the blocked plate six times with plate wash buffer, approximately 275 μL per well per wash. Aspirate the final wash and add 100 μL conjugate solution to each assay well.
8. Cover the plate and incubate at 25 EC for 1.5 hours.
9. Wash the blocked plate six times with plate wash buffer, approximately 275 μL per well per wash. Aspirate the final wash and add 100 μL substrate solution to each assay well.
10. Read the plate at 30 and 60 minutes in a fluorescence microtiter plate reader set at 365 nm excitation and 450 nm emission.

Biotinylation of Human Serum Albumin
  Materials:
  Human Serum Albumin: Sigma A 8763
  Sulfosuccinimidyl 6-(biotinamido)Hexanoate: Pierce 21335
    Tris base: Sigma T 1503
    20 mM sodium phosphate, pH 7.2
    100 mM sodium hydroxide solution
  Procedure:
  Human serum albumin is dissolved in phosphate buffer at a concentration of approximately 40 mg/mL. The protein concentration of the solution is determined by absorbance at 280 nm (1 mg/mL=OD280 of 0.58) or by the Lowry method.
  Immediately prior to biotinylation, the pH of the albumin solution is adjusted to 8.5 by the addition of sodium hydroxide. Succinimidyl biotin is then added at a molar ratio of 50:1 (422 mg succinimidyl biotin per mg albumin). The reaction mixture is vortexed thoroughly and then mixed gently for 45 minutes at ambient temperature.
  Reaction byproducts and unreacted biotin are removed by extensive dialysis against phosphate buffer. The biotinylated human serum albumin is stored at 4 C.

Preparation of Covalent Ready Cyanogen Bromide (CNBr) Activated Paper Discs
  Materials:
  Paper discs: Schleicher and Schuell 53870
  CNBr solution: 20 gm CNBr (Sigma C6388)+600 mL distilled water
    1M NaOH
    0.05M NaHCO3
    25%, 50%, 75%, and 100% acetone
    Distilled water
    Dessicant packets: Sigma S8394
    Zip lock plastic bags
  Procedure:
  The following procedure is performed under a hooded, well ventilated environment. 20 gm paper discs are swelled in 200 mL distilled water at room temperature. Swelled paper discs are then added to 600 mL of CNBr solution while stirring. Bring up the pH of the stirring mixture to 10.5 and maintain at pH 10.5 until 100 mL of 1M NaOH have been used up. Aspirate the resulting liquid and wash discs with 500 mL of NaHCO3 buffer for 2 minutes at room temperature. Repeat wash step×12. Rinse discs twice with 500 mL distilled water. Rinse discs twice with 500 mL 25% acetone. Rinse discs twice with 500 mL 50% acetone. Rinse discs twice with 500 mL 75% acetone. Rinse discs twice with 500 mL 100% acetone. Aspirate last acetone wash solution and allow discs to dry under a running fume hood at room temperature. Store dried CNBr activated paper discs in zip lock plastic bags containing dessicant packettes.

Preparation of Neutravidin Conjugated Paper Discs and Biotinylated Human Serum Albumin Conjugated Paper Discs
  Materials:
  Biotinylated human serum albumin: Prepared by method of Example 1
    Neutravidin: Pierce 31000
    CNBr-activated paper discs: Prepared by method of Example 2
    Modified Coca's buffer: 0.05M NaHCO3+0.15M NaCl, PH 7.2
    0.05M ethanolamine solution
    0.2M sodium acetate buffer, pH 4.0.
    Paper disc incubation buffer: 0.05M sodium phosphate+0.15M NaCl+0.05%NaN3+0.5% Tween20
  Procedure:
  A 2.5 mg/ml solution of neutravidin is prepared in modified Coca's buffer. A 2.5 mg/mL solution of biotinylated human serum albumin is prepared in modified Coca's buffer. 50 CNBr-activated discs are added to each mL of protein solution. Each protein/disc mixture is agitated for 16 to 18 hours at room temperature. Each solution surrounding the respective paper discs is aspirated and each set of discs are washed×3 with modified Coca's buffer. The washed discs are immersed in 0.05M ethanolamine solution and agitated for 3 hours in order to block any unreacted CNBr sites. Each set of paper discs is then washed×3 with the sodium acetate buffer. During the third step, the paper discs are incubated in the sodium acetate buffer for 30 minutes under gentle agitation. Each set of paper discs is then washed×4 in Coca's buffer and then stored in the paper disc incubation solution at 4 C.

Preparation of Neutravidin Coated Microtiter Plates
  Materials:
  Amino Polystyrene Microtiter Plates (White): Nunc 453686 or the equivalent
    Neutravidin: Pierce 31000
    Disuccinimidyl suberate (DSS): Pierce 21555
    Dimethyl sulfoxide (DMSO): Burdick and Jackson 081-1
    20 mM sodium phosphate, pH 5.50
    50 mM sodium carbonate, pH 9.6
    PBS with sodium azide
  Procedure:
  Prepare a volume of neutravidin appropriate for the number of plates to be coated. The coating solution contains 20 mg/mL neutravidin in 20 mM sodium phosphate, pH 5.50.

Prepare a suitable volume of DSS, 1.22 mg/mL, in dry DMSO. This solution must be used within 2 hours of preparation.

For each plate to be coated, add 60 mL DSS solution to each well followed by 60 mL of 50 mM sodium carbonate, pH 9.6. Incubate this mixture in the wells for 36 minutes at ambient temperature. Aspirate the wells and wash twice with deionized water. Immediately add 100 mL neutravidin solution. Cover the plate and incubate at ambient temperature for 16–18 hours.

Aspirate the coating solution and add approximately 280 mL PBS with azide to each well. Seal the plate with a foil cover. Store the coated plates at about 4 C.

Vaccination Methods

Methods for preparing and administering a vaccine using a peptide as an epitope have been reported. For example, Gilewski et al. (2000) used a MUC1 peptide with a keyhole limpet hemocyonin (KLM) in a conjugate to determine whether an immune response could be generated against the MUC1 peptide that would also bind with tumor cells. An immunogenic response was reported.

Passive Immunization Constructs that the Host Immune System Recognizes and Kills Cancer Cells

1. ENGINEERED ANTIGEN PRESENTING CELLS

See the "Detailed Description of the Invention" from U.S. Pat. No. 5,851,320, incorporated by reference.

2. DENDRITIC CELLS

See the "Detailed Description of the Invention" and "Examples 1–7" from U.S. Pat. No. 5,871,156 and the "Detailed Description of the Invention" and "Examples 1–5" from U.S. Pat. No. 6,080,409, incorporated by reference.

Active Immunization Using Cancer Vaccines

1. RECOMBINANT FUSION PROTEINS

See the "Summary of the Invention" from U.S. Pat. No. 4,399,216 and U.S. Pat. Nos. 6,106,829 and 5,616,477 incorporated by reference.

2. ADJUVANTS

See U.S. Pat. Nos. 5,750,110; 5,876,966; 5,876,735; 6,013,268 and 6,080,399, incorporated by reference.

3. NUCLEIC ACID MOLECULES

See U.S. Pat. Nos. 5,593,972; 5,817,637; 5,830,876; 6,063,384; 6,077,663; 5,981,505 and 5,942,235 incorporated by reference.

4. RECOMBINANT MICROORGANISMS WHICH EXPRESS CANCER ANTIGENS

See U.S. Pat. No. 6,051,237 incorporated by reference.

5. ANTIBODY DELIVERS ANTIGEN TO ANTIGEN PRESENTING CELLS

See U.S. Pat. 5,194,254 incorporated by reference.

6. HEAT SHOCK PROTEIN/ANTIGEN COMPLEXES

See U.S. Pat. Nos. 5,837,251; 5,981,706; 5,985,270; 5,997,873; 6,030,618 and 6,136,315 incorporated by reference.

7. CELL LYTIC THERAPEUTIC ANTIBODIES

See the section entitled "Therapy" in U.S. Pat. Nos. 4,585,742 incorporated by reference.

8. CELL ADHESION BLOCKING ANTIBODIES SUCH AS INTERGRIN ANTAGONISTS (See Kerr et al., 2000).

9. GROWTH FACTOR RECEPTOR BLOCKING ANTIBODIES

See U.S. Pat. No. 5,772,997 incorporated by reference.

Presence or Absence of 41 Molecules Listed in Table 3 in Prostate Cancer Peptides Information on the molecules in Table 3 were obtained from the following sources:

Bryden et al., 1999;
Cress et al., 1995;
Dong et al., 1996;
Fudge et al., 1994;
Giri et al., 1999;
Grasso et al., 1997;
Kimura et al., 1996;
Kramer et al., 1995;
Luo et al., 1999;
Rokhlin et al., 1997;
Takahashi et al., 1998;
Tozawa, 1996;
Tron et. al., 1999;
Watanabe et al., 1999; and
Zheng et al., 2000.

Use of Peptides of the Present Invention on Microchips

Microchips that have oligonucleotides or peptides have been developed by many groups or researches for various applications e.g. determining whether genes are present in a biological sample by determining whether DNA molecules in the sample hybridize under conditions wherein hybridization implies a specific degree of homology between a DNA molecule in a sample applied to the microchip and a DNA molecule in the microchip. Microchips are designed so that questions such as "Is the gene for the disease X present in a person?" or "Does the patient have a particular mutation?" or "Is there a specific antigen(s) present in the sample?" can be answered by interpreting the hybridization pattern in the chip, or in the case of antigen or antibody detection, the pattern of antigen-antibody complexing on the microchip. Examples of patents in the microchip area are U.S. Pat. No. 5,861, 247 and U.S. Pat. No. 5,770,721. Microchips are sold commercially by Affymetrix, Hyseq and other companies. Licenses are available for microchip technologies through Argonne National Laboratory.

DOCUMENTS CITED

Barratt (1998) *J. Immunother* 21(2):142–148.
Begum, N. A., et al. (1995) *Hepatology.* 22(5): 1447–1455.
Bogden and Moreau (1998) U.S. Pat. No. 5,736,517.
Bonkhoff, H. (1998), *Anal. Quant. Cytol. Histol.* 20(5): 437–442.
Boon, T. et al. (1994) U.S. Pat. No. 5,342,774.
Brame, C. J., et al. (1999) *J. Biol. Chem.* 274(19):13139–13146.
Bryden, et al. (1999) *BJU Int.* 84(9): 1032–1034.
Calenoff, E. (1998) U.S. Pat. No. 5,763,164.
Cheever (1997a) *Immunol Rev.* 157:177–194.
Cheever (1997b) *Adv. Cancer Res.* 71:343–371.
Cress, A F et al. (1995) *Cancer Metastasis Rev.* 1995 14(3):219–228.
Damiano, J. S., et al. (1999) *Blood* 93(5):1658–1656.
Damjanovich, L., et al. (1997) *Acta Chir Hung.* 36(1–4):69–71.
DeVita, V T, et al. (1985) *Cancer: Principles and Practice of Oncology*, $2^{nd}$ edition, Lippincott (Pub).
Disis et al. (1998a) *Immunology* 93(2): 192–199.
Disis et al. (1998b) *Crit Rev Immunol* 18(1–2):37–45.
Disis et al. (1999) *Clin Cancer Res.* 5(6):1289–1297.
Dong, J T, et al. (1996) *Cancer Res.* 56(19): 4387–4390.
Ekblom, M., et al. (1998) *Ann. N.Y. Acad. Sci.* 857:194–211.
Fauchere, J. L. and V. Pliska (1983) *Eur. J. Med. Chem.* 18(4):369–375.
Fleischmajer, R., et al. (1998) *Ann. U. U. Acad. Sci.* 857:212–227.
Fraga et al. (1990) *J. Mol. Recognit.* 3(2):65–7347.
Friedl, P., et al. (1998) *Cell Adhes. Commun.* 6(2–3): 225–236.

Fudge, K., et al. (1994) *Mod. Pathol.* 7(5):549–54.
Fujiwara, H., et al. (1998) *Harm. Res.* 50 Suppl 2:25t–29.
Furukawa, F., et al. (1994) *J. Dennatol.* 21(11):802–813.
Gilewski, et al. (2000) *Clin. Cancer Res.* 6(5):1693–1701.
Giri, D., et al. (1999) *Clin. Cancer Res.* 5(5):1063–1071.
Goldenberg, D. M. and H. A. Nabi (1999) *Semin. Nucl. Med.* 29(1):41–48.
Goldenberg, D. M. (1993) *Am. J. Med.* 94(3):297–312.
Grasso, A W, (1997) *Oncogene* 15(22):2705–2716.
Henderson et al. (1998) *J. Immunother* 21(4):247–256.
Hopp et al. (1981) *Prox. Natl. Acad. Sci. USA.* 78(6):3824–3828.
Hudziak (1998a) U.S. Pat. No. 5,772,997.
Hudziak (1998b) *Mol. Cell. Biol.* 9(3):1165–1172.
Hussain, R., et al. (1996). *Biomed. Petp. Proteins Nucleic Acids.* 2(3):67–70.
Katsura, M., et al. (1998) *Gynecol. Oncol.* 71(2):185–189.
Kerr et al. (2000) *Expert Opin. Investig Drugs* 9(6):1271–1279.
Kimura (1966)
Knight et al. U.S. Pat. No. 5,620,955.
Kramer et al. (1995) *J. Urol.* 154(5) 1636–1641.
Lhansi, F. A., et al. (1998) *J. Biol. Chem.* 273(12):6928–6936.
Lapis, H., et al. (1996) *Diagn. Mol. Pathol.* 5(2):127–135.
Lohi, J., et al. (1998) *J. Pathol.* 184(2):191–196.
Luguki, (1999)
Luo, W., et al. (1999) *Cancer Gene Ther.* 6(4):313–321.
Parker et al. (1986) *Biochemistry.* 25:5425–5432.
Rabinovitz, J., et al. (1995) *Clin. Exp. Metastasis* 13(6):481–491.
Rokhlin et al. (1997) *Cancer Res.* 57(9) 1758–1768.
Romonov, V. I. and Goligorsky, M. S. (1999) *Prostate* 39(2):108–118.
Ruoslahti, E. (1997) *Kidney Int.* 51(5):1413–1417.
Shamsi et al. (1998) *Radiology* 206(2):365–371.
Suzuki, K. and K. Takahashi (1999). *Int. J. Oncol.* 14(5):897–904.
Takahashi, S. et al. (1998) *Cancer Lett* 129(1): 97–102.
To, S. Y., et al. (1992) *J. Clin. Laser Med. Surg.* 10(3):159–169.
Tozawa, K. et al. (1996) *Nippon Hinyokika Gakkai Zasshi* 87(9):1082–1091.
Tran et al. (1999) *Am. J. Pathol.* 155(3) 797–798.
Tsimikas, S., et al. (1999) *J. Nucl. Cardiol.* 6(1Pt1):41–53.
Watanabe, M. et al. (1999) *Cancer Lett.* 141(1–2):173–178.
Zheng, D. Q., et al. (1999) *Cancer Res.* 59(7):1655–1664.
U.S. Pat. No. 4,399,216.
U.S. Pat. No. 4,585,742.
U.S. Pat. No. 5,194,254.
U.S. Pat. No. 5,593,972.
U.S. Pat. No. 5,616,477.
U.S. Pat. No. 5,750,110.
U.S. Pat. No. 5,770,721.
U.S. Pat. No. 5,817,637.
U.S. Pat. No. 5,830,876.
U.S. Pat. No. 5,837,251.
U.S. Pat. No. 5,861,247.
U.S. Pat. No. 5,871,756.
U.S. Pat. No. 5,876,735.
U.S. Pat. No. 5,876,966.
U.S. Pat. No. 5,942,235.
U.S. Pat. No. 5,962,320.
U.S. Pat. No. 5,981,505.
U.S. Pat. No. 5,981,706.
U.S. Pat. No. 5,985,270.
U.S. Pat. No. 5,997,873.
U.S. Pat. No. 6,013,268.
U.S. Pat. No. 6,030,618.
U.S. Pat. No. 6,051,237.
U.S. Pat. No. 6,063,384.
U.S. Pat. No. 6,077,663.
U.S. Pat. No. 6,080,399.
U.S. Pat. No. 6,080,409.
U.S. Pat. No. 6,106,829.
U.S. Pat. No. 6,136,315.

We claim:

1. A method for identifying candidate cancer-specific or cancer-associated antigens, said method comprising consecutively the steps of:

(a) obtaining an amino acid sequence of an extracellular domain of a receptor or receptor-like molecule;

(b) mapping hydrophilic regions of the domain by analyzing the amino acid sequence of the domain employing a rolling sum analysis of 7 consecutive residues;

(c) identifying the hydrophilic peptide regions of step (b) that contain amino acids susceptible to glycosylation;

(d) identifying amino acids in the hydrophilic peptide region of step (c) that are susceptible to modification other than glycosylation in the absence of steric hindrance by glycoside chains;

(e) synthesizing candidate peptides that comprise the amino acids identified in step (c) or identified in steps (c) and (d)

(f) labeling the candidate peptides at either end of their amino acid sequence; and (g) testing whether the candidate peptides are cancer-specific or cancer associated.

* * * * *

SEQUENCE LISTING

```
<160> NUMBER OF SEQ ID NOS: 68

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 1

Val Lys Xaa Ser Thr
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
```

```
<222> LOCATION: (3)
<223> OTHER INFORMATION: variable deglycosylated amino acid

<400> SEQUENCE: 2

Asp Lys Xaa Leu Ser
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)..(4)
<223> OTHER INFORMATION: variable deglycosylated amino acid

<400> SEQUENCE: 3

Asn Asn Xaa Xaa Ser Ser
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 4

Asp Lys Xaa Ser Thr
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 5

Gly Thr Xaa Lys Thr
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 6

Asp Arg Xaa Gly Thr
 1               5

<210> SEQ ID NO 7
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: variable deglycosylated amino acid

<400> SEQUENCE: 7

Xaa His Ser Glu Gly
  1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 8

Ser Pro Xaa His Ser
  1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 9

Asp Arg Xaa His Thr
  1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 10

Ser Asp Xaa Ser Thr
  1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 11
```

Phe Cys Xaa Arg Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 12

Lys Asn Xaa His Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 13

Ser Ala Xaa Arg Ser
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 14

Thr Arg Xaa Asp Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 15

Ser Lys Xaa Gln Ser
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide -continued

```
<221> NAME/KEY: MOD_RES
<222> LOCATION: (3)
<223> OTHER INFORMATION: variable deglycosylated amino acid

<400> SEQUENCE: 16

Pro Gly Xaa Arg Thr
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 17

Thr Lys Xaa Gly Thr
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 18

Lys Ile Xaa Ala Thr
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 19

Asp Ala Xaa Lys Thr
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (4)
<223> OTHER INFORMATION: variable deglycosylated amino acid

<400> SEQUENCE: 20

Pro Glu Arg Xaa Arg Thr
 1               5

<210> SEQ ID NO 21
```

-continued

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 21

Cys Arg Xaa Val Ser
 1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 22

Asp Thr Xaa Arg Ser
 1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 23

His Glu Xaa Cys Thr
 1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 24

Ala Glu Xaa Cys Thr
 1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 25
```

```
Pro Asp Xaa Cys Thr
1               5
```

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 26

```
Glu Ser Xaa Arg Thr
1               5
```

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 27

```
Glu Lys Xaa Gly Ser
1               5
```

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 28

```
Asp Ile Xaa Ser Ser
1               5
```

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 29

```
Val Gly Xaa Lys Ser
1               5
```

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic

```
                            peptide
<221> NAME/KEY: MOD_RES
<222> LOCATION: (3)
<223> OTHER INFORMATION: variable deglycosylated amino acid

<400> SEQUENCE: 30

Glu Glu Xaa Asn Ser
  1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 31

Lys Asp Xaa Arg Thr
  1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 32

Thr Arg Xaa Val Ser
  1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 33

His Lys Xaa Gln Thr
  1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 34

Gln Arg Xaa Ile Thr
  1               5
```

```
<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 35

Ser Glu Xaa Ala Ser
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 36

Asp Arg Xaa His Ser
 1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 37

Met Glu Xaa Lys Thr
 1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 38

Leu Glu Xaa His Thr
 1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid
```

```
<400> SEQUENCE: 39

Arg Met Xaa Ile Thr
 1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 40

Lys Ala Xaa Thr Ser
 1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 41

Leu Arg Xaa Glu Ser
 1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 42

Arg Ala Xaa His Ser
 1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 43

Gln Lys Xaa Gln Thr
 1               5

<210> SEQ ID NO 44
<211> LENGTH: 5
<212> TYPE: PRT
<213> ORGANISM: Artificial Sequence
<220> FEATURE:
```

-continued

```
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 44

Lys Gly Xaa Cys Ser
 1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 45

Gln Asp Xaa Lys Thr
 1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 46

Lys Ala Xaa Thr Thr
 1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 47

Thr Glu Xaa Gln Thr
 1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 48

Glu Lys Xaa Asp Thr
 1               5
```

```
<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 49

Asn Lys Xaa Val Thr
  1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 50

Val Thr Xaa Arg Ser
  1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: variable deglycosylated amino acid
<221> NAME/KEY: MOD_RES
<222> LOCATION: (5)
<223> OTHER INFORMATION: variable deglycosylated amino acid

<400> SEQUENCE: 51

Lys Xaa Val Thr Xaa Arg Ser
  1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 52

Lys Glu Xaa Ser Ser
  1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<221> NAME/KEY: MOD_RES
<222> LOCATION: (3)
<223> OTHER INFORMATION: variable deglycosylated amino acid

<400> SEQUENCE: 53

Glu Gln Xaa Cys Thr
 1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 54

Ser Lys Xaa Phe Ser
 1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 55

Arg Cys Xaa Gly Ser
 1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 56

Pro Asp Xaa Gln Thr
 1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 57

Gln Lys Xaa Ser Ser
 1               5

<210> SEQ ID NO 58
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 58

Glu Val Xaa Ser Ser
 1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 59

Ser Glu Xaa Asp Thr
 1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 60

Lys Glu Xaa Asp Thr
 1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 61

Gly His Xaa Glu Ser
 1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 62
```

Gly Asp Xaa Arg Thr
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 63

Asp Glu Xaa Ile Thr
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 64

Glu Tyr Xaa Thr Ser
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 65

Pro Asp Xaa Asp Thr
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: variable deglycosylated amino acid

<400> SEQUENCE: 66

Arg Asn Xaa Thr Thr
1               5

<210> SEQ ID NO 67
<211> LENGTH: 1210
<212> TYPE: PRT
<213> ORGANISM: Homo sapiens

<400> SEQUENCE: 67

-continued

```
Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Val Cys Gln
            20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gln Asn Met Tyr
            100                 105                 110

Tyr Glu Asn Ser Tyr Ala Leu Ala Val Leu Ser Asn Tyr Asp Ala Asp
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asp Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asp
            340                 345                 350

Ala Thr Asn Ile Lys His Phe Lys Asp Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asp Arg Thr Asp
                405                 410                 415
```

-continued

Leu His Ala Phe Glu Asn Leu Glu Ile Ile Arg Gly Arg Thr Lys Gln
            420                 425                 430

His Gly Gln Phe Ser Leu Ala Val Val Ser Leu Asp Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asp
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asp Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asp Asn Thr Leu Val Trp
        595                 600                 605

Lys Tyr Ala Asp Ala Gly His Val Cys His Leu Cys His Pro Asp Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro

-continued

```
                835                 840                 845
Gln His Val Lys Ile Thr Asp Phe Gly Leu Ala Lys Leu Leu Gly Ala
    850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
        915                 920                 925
Lys Gly Glu Arg Leu Pro Gln Pro Pro Ile Cys Thr Ile Asp Val Tyr
    930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
Thr Asp Ser Asn Phe Tyr Arg Ala Leu Met Asp Glu Glu Asp Met Asp
        995                 1000                1005
Asp Val Val Asp Ala Asp Glu Tyr Leu Ile Pro Gln Gln Gly Phe Phe
    1010                1015                1020
Ser Ser Pro Ser Thr Ser Arg Thr Pro Leu Leu Ser Ser Leu Ser Ala
1025                1030                1035                1040
Thr Ser Asn Asn Ser Thr Val Ala Cys Ile Asp Arg Asn Gly Leu Gln
                1045                1050                1055
Ser Cys Pro Ile Lys Glu Asp Ser Phe Leu Gln Arg Tyr Ser Ser Asp
            1060                1065                1070
Pro Thr Gly Ala Leu Thr Glu Asp Ser Ile Asp Asp Thr Phe Leu Pro
        1075                1080                1085
Val Pro Glu Tyr Ile Asn Gln Ser Val Pro Lys Arg Pro Ala Gly Ser
    1090                1095                1100
Val Gln Asn Pro Val Tyr His Asn Gln Pro Leu Asn Pro Ala Pro Ser
1105                1110                1115                1120
Arg Asp Pro His Tyr Gln Asp Pro His Ser Thr Ala Val Gly Asn Pro
                1125                1130                1135
Glu Tyr Leu Asn Thr Val Gln Pro Thr Cys Val Asn Ser Thr Phe Asp
            1140                1145                1150
Ser Pro Ala His Trp Ala Gln Lys Gly Ser His Gln Ile Ser Leu Asp
        1155                1160                1165
Asn Pro Asp Tyr Gln Gln Asp Phe Phe Pro Lys Glu Ala Lys Pro Asn
    1170                1175                1180
Gly Ile Phe Lys Gly Ser Thr Ala Glu Asn Ala Glu Tyr Leu Arg Val
1185                1190                1195                1200
Ala Pro Gln Ser Ser Glu Phe Ile Gly Ala
                1205                1210
```

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: synthetic peptide -continued

```
<221> NAME/KEY: MOD_RES
<222> LOCATION: (4)
<223> OTHER INFORMATION: variable deglycosylated amino acid

<400> SEQUENCE: 68

Ala Glu Met Xaa Gly Ser Lys
 1               5
```